(12) United States Patent
Thanavala

(10) Patent No.: US 10,738,119 B2
(45) Date of Patent: Aug. 11, 2020

(54) COMBINATION THERAPY FOR HEPATOCELLULAR CARCINOMA

(71) Applicant: Health Research, Inc., Buffalo, NY (US)

(72) Inventor: Yasmin Thanavala, Williamsville, NY (US)

(73) Assignee: Health Research, Inc., Buffalo, NY (US)

( * ) Notice: Subject to any disclaimer, the term of this patent is extended or adjusted under 35 U.S.C. 154(b) by 291 days.

(21) Appl. No.: 15/120,036

(22) PCT Filed: Feb. 18, 2015

(86) PCT No.: PCT/US2015/016317
§ 371 (c)(1),
(2) Date: Aug. 18, 2016

(87) PCT Pub. No.: WO2015/126903
PCT Pub. Date: Aug. 27, 2015

(65) Prior Publication Data
US 2018/0162941 A1    Jun. 14, 2018

Related U.S. Application Data

(60) Provisional application No. 61/941,020, filed on Feb. 18, 2014.

(51) Int. Cl.
| | | |
|---|---|---|
| *C12N 15/85* | (2006.01) | |
| *A61K 39/395* | (2006.01) | |
| *C07K 16/28* | (2006.01) | |
| *A61K 31/44* | (2006.01) | |
| *A61K 45/06* | (2006.01) | |
| *A61K 35/15* | (2015.01) | |
| *A61P 35/00* | (2006.01) | |
| *G01N 33/574* | (2006.01) | |

(52) U.S. Cl.
CPC .......... *C07K 16/2818* (2013.01); *A61K 31/44* (2013.01); *A61K 35/15* (2013.01); *A61K 39/3955* (2013.01); *A61K 45/06* (2013.01); *A61P 35/00* (2018.01); *G01N 33/57438* (2013.01); *C07K 2317/76* (2013.01); *G01N 2333/70521* (2013.01)

(58) Field of Classification Search
None
See application file for complete search history.

(56) References Cited

U.S. PATENT DOCUMENTS

| | | |
|---|---|---|
| 2012/0108641 A1 | 5/2012 | Demers et al. |
| 2013/0034559 A1 | 2/2013 | Queva et al. |
| 2013/0202623 A1 | 8/2013 | Chomont et al. |

FOREIGN PATENT DOCUMENTS

WO    2013173223    11/2013

OTHER PUBLICATIONS

Chen et al., ( Inter.J Cancer, 2014, v.134, pp. 319-331.*
Hsu et al., ( Liver Intern, 2010, v.30, pp. 1379-1386).*
Chen et al., Sorafenib relieves cell-intrinsic and cell-extrinsic inhibitions of effector T cells in tumor microenvironment to augment antitumor immunity, International Journal of Cancer, vol. 134, pp. 319-331. Jul. 2, 2013.
Nexavar Dosage, pp. 1-3, retrieved from the internet (www.drugs.com/dosage/nexavar.html) on May 8, 2015. May 8, 2012.
Masters et al., Antitumor activity of anti-PD-1 in combination with tyrosine kinase inhibitors in a preclinical renal cell carcinoma model, Proceedings of the 105th Annual Meeting of the Amer. Assoc. for Cancer Research, vol. 74, Abstract No. 5016. Apr. 9, 2014.
Wang et al., Combinatorial immunotherpay of sorafenib and blockade of programmed death-ligand 1 induces effective natural killer cell responses against hepatocellular carcinoma, Tumor Biology, vol. 36, Iss. 3, pp. 1561-1566. Nov. 5, 2014.
Kalathil et al., Higher Frequencies of GARP+CTLA-4+Foxp3+ T Regulatory Cells and Myeloid-Derived Suppressor Cells in Hepatocellular Carcinoma Patients Are Associated with Impaired T-Cell Functionality, Cancer Res. 2013; 73:2435-24444. Feb. 19, 2013.
Thomas Reiberger, CXCR4 inhibition in combination with anti-PD1 immunotherapy results in an effective immune response during treatment with sorafenib in hepatocellular carcinoma, American Association for the Study of Liver Diseases, Nov. 9, 2014, 60966, URL: https://liverlearning.aasld.org/aasld/2014/thelivermeeting/60966/ Nov. 9, 2014.
Wang et al., Sorafenib-induced acute-on-chronic liver failure in a patient with hepatocellular carcinoma after transarterial chemoembolization and radiofrequency ablation: A case report, Molecular and Clinical Onology, vol. 7, No. 4, pp. 693-695 Aug. 3, 2017.
De Martin et al., Characterization of liver injury induced by cancer immunotherapy using immune checkpoint inhibitors, Journal of Hepatology, vol. 68, No. 6, pp. 1181-1190 Jun. 1, 2018.

* cited by examiner

*Primary Examiner* — Michail A Belyavskyi
(74) *Attorney, Agent, or Firm* — Hodgson Russ LLP

(57) ABSTRACT

Provided are methods and compositions for a combination therapy for liver disorders such as hepatocellular carcinoma. Also provided is a method for determining the effectiveness of therapy involving tyrosine kinase inhibitors such as sorafenib. The method comprises determining the status of PD-1 on T cells, and based on a change in the level of PD-1 on certain cells, a determination of the effectiveness of the tyrosine kinase, and an indication for a combination therapy comprising a lower dose of tyrosine kinase inhibitor and a PD-1 inhibitor can be made.

9 Claims, 21 Drawing Sheets

HCC patients with decrease in PD-1 levels after sorafenib treatment

COMBINATION THERAPY FOR HEPATOCELLULAR CARCINOMA

CROSS-REFERENCE TO RELATED APPLICATIONS

This application claims priority to provisional patent application No. 61/941,020 filed Feb. 18, 2014, the disclosure of which is incorporated herein by reference.

FIELD OF THE DISCLOSURE

This disclosure relates to a combination therapy using a tyrosine kinase inhibitor and PD-1 inhibitor.

BACKGROUND OF THE DISCLOSURE

Hepatocellular carcinoma (HCC) is the fifth-most common cancer in the world and the third highest cause of cancer-related mortality globally. HCC develops in patients with chronic hepatitis, either due to chronic hepatitis B or C viral infection or due to inflammation following aflatoxin ingestion, or excessive alcohol consumption. Unfortunately, most HCC patients are first diagnosed with the disease at an advanced stage or present with poor liver function, thereby preventing the use of potentially curative therapies. Thus, treatment options for patients with advanced stage disease are limited to either chemoembolization or systemic therapies, which include sorafenib an oral anti-angiogenic agent that is the current backbone of HCC therapy. Though these approaches have led to improved clinical outcomes, patients remain at high risk of disease recurrence after potentially curative surgery and ablation, and survival remains less than one year for patients with advanced stage disease. As toxic chemotherapies are often not well-tolerated by these patients due to liver dysfunction, novel immune-based therapies such as anti-tumor vaccination and adoptive transfer of tumor-specific cytotoxic T cells (CTL) hold promise; however, their impact on tumor regression remains limited. The lack of efficacy of such therapies implies that HCC has developed multiple strategies of escaping tumor-specific immunity. Developing efficacious immunotherapies for HCC is challenging for clinicians.

SUMMARY OF THE DISCLOSURE

This disclosure provides methods and compositions for identifying likelihood of favorable outcome of tyrosine kinase (TK) inhibitor therapy in liver disorders, such as HCC. This disclosure also provides a combination therapy for individuals who have a favorable prognosis with a TK inhibitor.

We evaluated HCC patients and quantified the cumulative frequency of T regulatory cells (Tregs), exhausted $CD4^+$ helper T cells, and myeloid-derived suppressor cells (MDSC) to gain an understanding of the overall level of immune dysfunction in inoperable patients. We documented augmented numbers of Tregs, MDSC, $PD-1^+$ exhausted T cells and increased levels of immunosuppressive cytokines in HCC patients, compared to normal controls, revealing a network of potential mechanisms of immune dysregulation in HCC patients. We demonstrated that combined regimens to deplete Tregs, MDSC, and $PD-1^+$ T cells in advanced HCC patients restored production of granzyme B by $CD8^+$ T cells, reaching levels observed in normal controls, and also modestly increased the number of IFN-γ producing $CD4^+$ T cells.

We also evaluated HCC patients who were being treated with a tyrosine kinase inhibitor—sorafenib. In some of these patients, we unexpectedly observed that PD-1 levels on certain types of T cells were decreased. Further, and importantly, we observed that the patients in which PD-1 levels were decreased had longer survival times compared to those patients on sorafenib who did not exhibit a decrease in PD-1 levels.

Based on our findings, the present disclosure provides compositions and methods for treatment of liver disorders such as hepatocellular carcinoma and liver cirrhosis. The method comprises therapies for restoring T cell function, which may include reducing suppressor T-cell function.

In one embodiment, the method is a combination therapy comprising administration of kinase inhibitors (such as tyrosine kinase inhibitor) with one or more PD-1 inhibitors. In one embodiment, the combination therapy comprises administration of sorafenib and an anti-PD-1 antibody.

In one embodiment, the administration of a PD-1 inhibitor enables reducing the effective dose of the TK inhibitor required to produce the same effect as the TK inhibitor alone. For example, the maximal level of sorafenib for a HCC patient may be decreased by adding a PD-1 inhibitor to the treatment regimen.

In one embodiment, the present disclosure also provides a method for prognosis of HCC patients who are on sorafenib therapy. The method comprises evaluating the status of PD-1 in these patients. A reduction in PD-1 levels is indicative of the effectiveness of the sorafenib therapy for that individual.

The present disclosure also provides compositions and kits comprising a TK inhibitor and a PD-1 inhibitor. In one embodiment, the composition and the kit comprises sorafenib and a PD-1 antibody. The kit may comprise a supply for a first dosage of sorafenib and a supply for a second dosage of sorafenib, wherein the second dosage is lower than the first. The kit may also comprise a supply of PD-1 inhibitor. The PD-1 inhibitor and the second dosage of sorafenib may be provided as a single composition or may be provided separately. The kit may further comprise instructions for treatment regimens of the two inhibitors, and optionally administration devices.

BRIEF DESCRIPTION OF THE FIGURES

(FIG. 1A, FIG. 1B) Representative staining from an individual HCC patient and normal healthy donor for the frequency of $CD3^+CD4^+Foxp3^+$ T cells. (FIG. 1C) Frequency and (FIG. 1D) absolute number of cells/ml of $CD4^+Foxp3^+$ Tregs in peripheral blood of HCC patients and normal healthy subjects. (FIG. 1E, FIG. 1F) Representative staining of GARP on $CD3^+CD4^+Foxp3^+$ T cells. (FIG. 1G) Frequency of $GARP^+$ Tregs and (FIG. 1H) GARP expression levels measured by mean fluorescent intensity (MFI) on Tregs. (FIG. 1I, FIG. 1J) Representative staining of CTLA-4 on $CD3^+CD4^+Foxp3^+$ T cells. (FIG. 1K) Frequency of $CTLA-4^+$ Tregs and (FIG. 1L) CTLA-4 expression levels. Each symbol represents an individual HCC patient (●) or normal healthy subjects (□); lines represent median values for the group. $*P<0.05$, $P<0.01$, $*P<0.001$, Mann-Whitney U test; $†P<0.05$ Hochberg adjustment for multiple comparison.

(FIG. 2A, FIG. 2B) Representative staining of $HLA-DR^-$ CD14⁻CD11b⁺CD33⁺ MDSC from one HCC patient and one normal healthy donor. (FIG. 2C) Frequency and (FIG. 2D) absolute number of cells/ml of MDSC in the peripheral blood of HCC patients and healthy donors. (FIG. 2E) Correlation of CD11b⁺CD33⁺ MDSC frequency and CD4⁺Foxp3⁺ Treg frequency. Each symbol represents an individual HCC patient (●) or normal healthy subjects (□); lines represent median values for the group. *P<0.05, P<0.01, *P<0.001, Mann-Whitney U test; †P<0.05 Hochberg adjustment for multiple comparison.

(FIG. 3A-3C) Cytokine-specific sandwich ELISA of plasma from HCC patients and healthy normal subjects were assayed in order to measure levels of circulating IFN-γ, IL-10, and TGF-β1. (FIG. 3D) Correlation of TGF-β1 plasma levels and frequency of CD4⁺Foxp3⁺ Tregs. Each symbol represents an individual HCC patient (●) or normal healthy subjects (□); lines represent median values for the group. P<0.01, *P<0.001, Mann-Whitney U test; †P<0.05 Hochberg adjustment for multiple comparison.

(FIG. 4A) Frequency of PD-1⁺CD4⁺ T cells and (FIG. 4B) PD-1 expression levels on CD4⁺ T cells. (FIG. 4C) Representative CD4⁺ T cell and (FIG. 4D) CD8⁺ T cell proliferation measured by CFSE dilution in an HCC patient pre-depletion (□) and post-depletion (■) of suppressor cells and a normal healthy donor (□). (FIG. 4E) CD4⁺ T cell and (FIG. 4F) CD8⁺ T cell proliferation index for PHA and (FIG. 4G) CD4⁺ T cell and (FIG. 4H) CD8⁺ T cell proliferation index for anti-CD3/anti-CD28 stimulation. Each symbol represents an individual HCC patient pre-depletion (●), post-depletion (○), or normal healthy subjects (□); lines represent median values for the group. *P<0.05, P<0.01, *P<0.001, Mann-Whitney U test; †P<0.05 Hochberg adjustment for multiple comparison.

(FIG. 6A) q-PCR analysis of Foxp3 gene expression from PBMCs of HCC patients (n=10) and healthy donors (n=10). Lines represent mean values of Foxp3 mRNA copies normalized to GAPDH control (**P=0.005). (FIG. 6B) Correlation between Foxp3 mRNA copies and CD4⁺FoxP3⁺ Treg frequency (Spearman correlation=0.49; P=0.005).

(FIG. 8E, FIG. 8F) Frequency of CTLA-4 expressing CD4⁺Foxp3⁺ Tregs and (FIG. 8G, FIG. 8H) expression levels of CTLA-4 on CD4⁺Foxp3⁺ Tregs was also compared. Each symbol represents an individual HCC patient (,) or normal healthy subjects ( ) lines represent median values for the group.

(FIG. 9A, FIG. 9B) Frequency as well as (FIG. 9C, FIG. 9D) absolute number of MDSC in the peripheral blood of HCC patients was compared after stratification of patients based on exposure to HCV infection or prior treatment. Each symbol represents an individual HCC patient ( ) or normal healthy subjects ( ) lines represent median values for the group.

(FIG. 10A) Phenotypic analysis of plasmacytoid DCs (Lin-CD11clowCD123⁺) from a representative HCC patient and (FIG. 10B) a healthy subject. (FIG. 10C, FIG. 10D) HLA-DR and CD86 expression was evaluated on CD11c⁺CD123⁺ cell population. (FIG. 10E) Frequency as well as (FIG. 10F) absolute number of pDC in the peripheral blood of HCC patients (n=23) and healthy donors (n=20) (*P<0.05, **P<0.01). Each symbol represents an individual HCC patient (circles) or normal healthy subjects (□); lines represent median values for the group.

(FIGS. 11G-11I) granzyme B expression in CD8⁺ T cells from the same subjects stimulated with PHA.

(FIG. 14A) Frequency of PD-1⁺CD4⁺ T cells (FIG. 14B) PD-1 expression levels (MFI) on CD4⁺ T cells (n=19). (FIG. 14C) Frequency of PD-1⁺Foxp3⁺ T cells (n=19). (FIG. 14D) Frequency of PD⁺CD8⁺ T cells. (FIG. 14E) Absolute number of PD-1⁺CD8⁺ T cells (n=19) and (FIG. 14F) PD-1 expression levels (MFI) on CD8⁺ T cells. Each symbol represents an individual HCC patient pre (■) or post sorafenib treatment (●); lines represent mean values for the group. *P<0.05, Permutation t-test.

(FIG. 16A) Frequency and (FIG. 16B) absolute numbers of $CD4^+Foxp3^+$ Tregs in the peripheral blood of HCC patients (n=19). (FIG. 16C) Frequency and (FIG. 16D) absolute numbers of $CTLA-4^+$ Tregs in HCC patients (n=19). (FIG. 16E) Frequency and (FIG. 16F) absolute numbers of MDSC in HCC patients (n=19). Each symbol represents an individual HCC patient pre (■) or post sorafenib treatment (●); lines represent mean values for the group. *P<0.05, Permutation t-test.

(FIG. 19A) frequency of $CD4^+Foxp3^+$ Tregs (FIG. 19B) absolute number of $CD4^+Foxp3^+$ Tregs (FIG. 19C) frequency of $CD4^+Foxp3^+$ $CTLA-4^+$ Tregs (FIG. 19D) absolute number of $CTLA-4^+Foxp3^+$ Tregs (FIG. 19E) frequency of $CD4^+PD-1^+$ T cells (FIG. 19F) expression levels of PD-1 (MFI) on $CD4^+$ T cells (FIG. 19G) frequency of $CD4^+Foxp3^+PD-1^+$ T cells (FIG. 19H) frequency of $CD8^+PD-1^+$ T cells (FIG. 19I) absolute number of $CD8^+PD-1^+$ T cells (FIG. 19J) expression levels of PD-1 (MFI) on $CD8^+$ T cells (FIG. 19K) frequency of $CD11b^+CD33^+$ MDSC (FIG. 19L) absolute number of $CD11b^+CD33^+$ MDSC. Each symbol represents an individual HCC patient pre and post sorafenib treatment (●).

DETAILED DESCRIPTION OF THE DISCLOSURE

Figure 1:
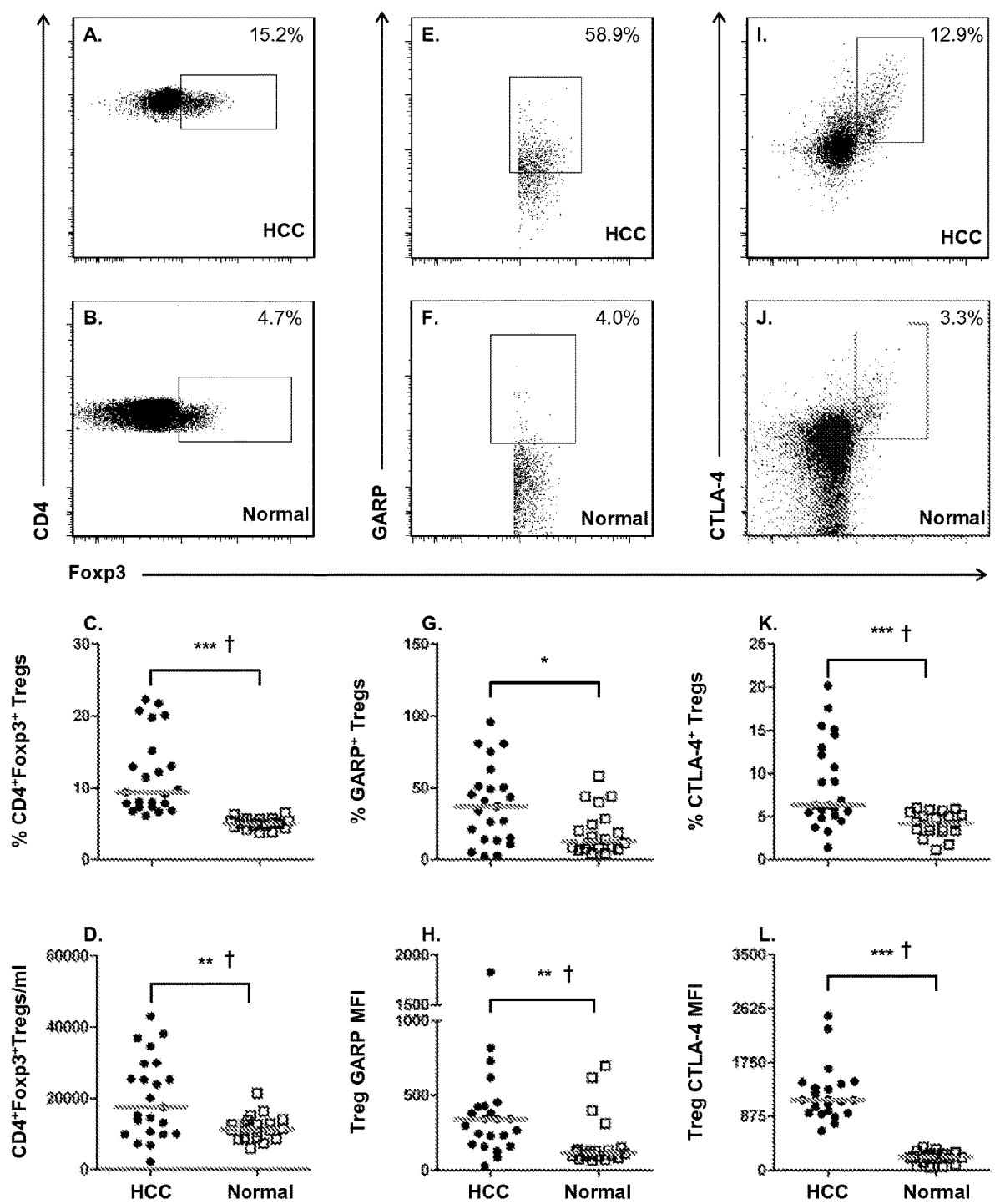
FIGS. 1A-1L. Increased numbers of GARP and CTLA-4 expressing Tregs in HCC patients. Flow cytometric analysis was performed on PBMCs from HCC patients (n=23) and healthy controls (n=20).

The present disclosure provides methods, compositions and kits for determining the efficacy of treatment for liver disorders. The disclosure also provides methods, compositions and kits for a combination therapy for liver disorders.

The present disclosure provides data indicating altered profile for several T cell markers in HCC. The data demonstrate an increase in $Foxp3^+$, $GARP^+$, $CTLA-4^+$ T regs, MDSC, and $PD-1^+$ exhausted T cells, as well as certain immunosuppressive cytokines like IL-10 and TGFβ. Further, we observed that in some advanced HCC patients being treated by the tyrosine kinase inhibitor sorafenib, a reduction in PD-1 levels correlated favorably with longer survival times. Thus, in one embodiment, evaluating and modulating PD-1 levels can be used for both prognostic and therapeutic purposes. Based on these findings, the present disclosure provides methods and compositions for combination therapy for hepatocellular carcinoma and for prognosis of therapy with tyrosine kinase inhibitors.

The present findings indicate combining sorafenib treatment with anti-PD-1 therapy will have clinical benefit. Furthermore, the phenotype and functional activity of T cells measured after sorafenib treatment can serve as a predictive biomarker capable of identifying HCC patients most likely to benefit from a continuation of treatment with sorafenib alone or a combination therapy of sorafenib with a PD-1 inhibitor. Thus, in one embodiment, these biomarkers are used in patient selection and therapeutic optimization.

The present study represents the first demonstration that therapy using sorafenib resulted in statistically significant reduction of $PD-1^+CD4^+$ T cells in a subset of HCC patients. Patients with a greater decrease in the number of $PD-1^+$ $CD4^+$ T cells or $PD-1^+CD8^+$ T cells after therapy showed significant correlation with overall survival and had a better prognosis. Therefore, in one embodiment, PD-1 status can be used as a signature immune biomarker which can predict the clinical efficacy of anti-angiogenic therapy in HCC patients.

The present study also demonstrates that anti-angiogenic therapy using sorafenib resulted in a significant reduction in the number of circulating Tregs and this correlated with overall survival of HCC patients. Previous studies using sorafenib in renal carcinoma patients (Desar et al., Int. J. cancer 129:507-512, 2011) or sunitinib (Finke et al., Clin. Cancer Res., 14:6674-6682, 2008) could not achieve significant association between any of the immune parameters investigated or could not achieve statistical significance.

Therefore, in one embodiment, numbers of circulating Tregs can be determined to evaluate the efficacy of sorafenib and for prognosis if sorafenib treatment is continued. If a decrease in the numbers or circulating Tregs is observed after the first sorafenib treatment regimen, a second treatment regimen can be initiated where sorafenib dosage is reduced and/or given in combination with a PD-1 inhibitor.

In our study HCC patients with greater decrease either in the percentage or absolute number of MDSC after sorafenib treatment had a better prognosis as quantified based on Accelerated Failure Time (AFT) models. Therefore, in one embodiment, MDSC levels can be determined to evaluate the efficacy of sorafenib and for prognosis if sorafenib treatment is continued. If a decrease in the numbers or percentage of MDSCs is observed after the first sorafenib treatment regimen, a second treatment regimen can be initiated where sorafenib dosage is reduced and given in combination with a PD-1 inhibitor.

In addition to a decline in Treg levels after sorafenib treatment we also detected significant decrease in the levels of Treg derived cytokines IL-10 and TGF-3 in the plasma of HCC patients. TGF-β1 blunts anti-tumor immune functions of differentiated TH1 cells and fully differentiated cytotoxic T cells within the tumor microenvironment. Increased quantities of TGF-β1 in the tumor and tumor microenvironment promote tumorigenesis by down regulation of immune surveillance mechanism, thereby making TGF-β1 a potential druggable target. We observed significant increase in the levels of plasma IFN-γ in HCC patients after sorafenib treatment. Therefore, in one embodiment, levels of plasma IFN-γ can be determined to evaluate the efficacy of sorafenib and prognosis if sorafenib treatment is continued. If an increase in plasma IFN-γ are observed after the first sorafenib treatment regimen, a second treatment regimen can be initiated where sorafenib dosage is reduced and given in combination with a PD-1 inhibitor.

In one embodiment, administration of sorafenib can be used as an adjunct in combination with immunotherapeutic approaches to enhance the therapeutic efficacy of immune based strategies against advanced malignancies. In one embodiment, Tregs, MDSC and PD-1$^+$ T cells are monitored after sorafenib treatment to serve as a predictive biomarker for identifying HCC patients most likely to benefit from this treatment. Therefore, in addition to patient selection, these biomarkers can be used for therapeutic optimization.

In one aspect, the method provides a method for alleviating HCC (including advanced HCC) in patients, comprising the steps of interfering with or dampening the function of Tregs, MDSC, or PD-1$^+$ T cells or combinations thereof. In one embodiment, the dampening of Tregs, MDSC, or PD-1$^+$ T cells is carried out by administration of a PD-1 inhibitor.

The term "PD-1 inhibitor" as used herein means any agent that interferes or blocks the binding of PD-1 receptor (generally referred to simply as PD-1) on T cells with its ligands, PD-L1 and PD-L2, which are present on tumor cells. The PD-1 inhibitor may be an antibody or a fragment thereof which interferes with, inhibits, or blocks the PD-1 binding to its ligands. A PD-1 inhibitor may also be a small molecule or any other agent.

The term "PD-1 levels" as used herein means the level of expression of PD-1 on T cells or the percent of PD-1 positive T cells that are also CD4$^+$ or CD8$^+$ expressed as a percent of the total number of CD4$^+$ or CD8$^+$ cells. The level of expression of PD-1 on T cells can be determined by any standard method. For example, it can be determined by flow cytometry and measured as mean fluorescence intensity (MFI).

In one embodiment, the disclosure provides a method for a combination therapy for individuals diagnosed with HCC comprising administering to the individual a tyrosine kinase inhibitor and an inhibitor of PD-1. The TK inhibitor and the PD-1 inhibitor may be administered simultaneously or contemporaneously, as a single composition or separate compositions, or the TK and PD-1 inhibitors may be administered at different times.

In one embodiment, the method comprises administering a PD-1 inhibitor to an individual who is already on a TK inhibitor regimen. In one embodiment, the TK inhibitor treatment regimen is continuing when the PD-1 regimen is started. In one embodiment, the TK inhibitor regimen may have been completed or interrupted when the PD-1 regimen is started.

In one embodiment, the method comprises administration of one or more TK inhibitors to an individual for a suitable period of time, testing to see if PD-1 levels (expression of PD-1, such as measured as MFI in flow cytometry or percent of PD-1 positive CD4$^+$ or CD8$^+$ T cells) are affected as compared to reference controls, and if PD-1 levels are lower than controls, then administering the TK inhibitor with one or more PD-1 inhibitor. The reference controls may be levels from normal individuals or may be PD-1 levels in the individual being treated prior to initiation of sorafenib treatment.

In one embodiment, the method comprises administration of a first dosage of sorafenib to an individual diagnosed with HCC for a suitable period of time (such as from 1 to 20 weeks and all weeks and days therebetween), testing to see if PD-1 levels are reduced (compared to a reference control), and if reduced, administering to the individual a lower dosage of sorafenib in combination with an PD-1 inhibitor. In a variation of this embodiment, the method comprises determining PD-1 levels prior to, or early in the regimen for first dosage of sorafenib treatment. After a suitable period of time, PD-1 levels are determined, and if the levels are reduced compared to the levels prior to or at the beginning of sorafenib treatment, then a combination therapy of a sorafenib and PD-1 inhibitor is initiated. In one embodiment, in the combination therapy, the dosage of sorafenib is lower (second dosage) than the initial dosage administered in the absence of PD-1 inhibitor. In one embodiment, the second dosage of sorafenib is 50 to 95% (and all integers therebetween) of the first dosage. PD-1 levels can be monitored throughout sorafenib treatment and/or before or after initiation or termination of the treatment.

In one embodiment, the reduction in PD-1 levels is at least 5%. In one embodiment, the reduction in PD-1 levels is from 10-50% and all percentages therebetween. In one embodiment, the reduction in PD-1 levels is more than 50%.

The TK inhibitor may be any inhibitor known for use in HCC treatment. For example, the TK inhibitor may be sorafenib, sunitib, tivozanib and the like. Sorafenib is currently commonly used for HCC treatment. The TK inhibitor may be used as a pharmaceutically acceptable salt which means it retains the desired biological activity of the parent compound and does not impart any unacceptable toxic effects. Examples of such salts include acid and basic salts. Examples include those derived from inorganic acids, organic acids and the like. Basic salts include sodium, potassium, magnesium, calcium, N,N'-dibenzylethylenediamine, N-methylglucamine, chloroprocaine, choline, diethanolamine, ethylenediamine, tosyl and the like.

Inhibitors of PD-1 include antibodies to PD-1. Antibodies to PD-1 are known in the art and include MK-3475 (KEYTRUDA, also known as pembrolizumab), BMS-936558 (OPIDIVO, also known as nivolumab). Inhibitors of PD-1 also include antibodies to PD-1 ligands (anti-PDL1). For example, MPDL3280A from Roche and BMS-936559 can be used.

The inhibitor of PD-1 may be used labeled or unlabeled. For example, it may be covalently or noncovalently labeled with a fluorophore, a quantum dot, a phosphore, a chemiluminescent compound, a bioluminescent compound, a chromogenic compound, or a detectable isotope such as a radioisotope, a biotin or avidin molecule, or any other label known in the art. The PD-1 inhibitor may be labeled before or after contact with the sample. PD-1 inhibitor may be detected by a labeled second antibody or by magnetic beads.

In one embodiment, the sample from the patient for determination of PD-1 levels is a biological fluid sample comprising a population of T cells. In one embodiment, the sample is whole blood, serum or plasma. In one embodiment, the sample comprises PBMCs. In one embodiment, the sample is enriched for PBMCs—such as using density gradient methodologies. In one embodiment, a sample comprising PBMCs (or enriched for PBMCs) may be further enriched for T cells or particular types of T cells such as $CD4^+$ and/or $CD8^+$cells. This can be done by using, for example, CD4 or CD8 affinity molecules. T cells or PBMCs may also be first expanded in vitro and then used.

To evaluate the status of PD-1 on T cells, a sample comprising a population of T cells is contacted with a detectable molecule which can bind to PD-1 on the T cells. The detectable molecule may be itself labeled or may be detectable by using a secondary labeled molecule. The detectable molecule may be an antibody to PD-1 or may be a ligand of PD-1. In one embodiment, following specific binding of the detectable molecule to PD-1, the PD-1/detectable molecule complex can be detected. In one embodiment, the method also comprises determining if the cells are also $CD4^+$ and/or $CD8^+$ by using detectable molecules that bind to CD4 and CD8. Detection of such complexes (such as PD-1/detectable molecules and/or CD4 or CD8/detectable complexes) may be done by methods based on fluorescence, bioluminescence, chemiluminescence, spectroscopic, photochemical, biochemical, immunochemical, chemical, magnetic, or other physical means known to one of ordinary skill in the art. In one embodiment, the detection may be carried out using flow cytometry using fluorescence-activated cell sorting (FACS) or magnetic-activated cell sorting (MACS).

In one embodiment, detection of PD-1 on T cells is carried out in conjunction with other T cell markers. For example, in one embodiment, PD-1 status is determined on T cells which are also positive for CD4 and/or CD8. Detection of PD-1 and $CD4^+$ or $CD8^+$ can be carried out using flow cytometry.

In one embodiment, instead of or in addition to determining PD-1 status on T cells (such as CD4 or CD8 cells), the number of $Foxp3^+$ Tregs may be determined. If the number is decreased, then the likelihood of favorable outcome is increased and a combination therapy of sorafenib and PD-1 inhibitor may be instituted. In one embodiment, the numbers of MDSCs may be determined and if a decrease in the numbers is observed after sorafenib treatment, then the likelihood of favorable outcome is increased and a combination therapy of sorafenib and PD-1 inhibitor may be initiated.

In one embodiment, the method comprises determining which individuals undergoing treatment for HCC with a TK inhibitor would be suitable for receiving PD-1 inhibitor. The method comprises determining if $PD-1^+CD4^+$ or $PD-1^+$ $CD8^+$ T cells and/or level of PD-1 expression is increased, and if such increase is observed (compared to a reference value), then identifying the individual as suitable for administration of PD-1 inhibitor.

Progress of PD-1 inhibitor treatment can be followed in individuals (humans or non-human animals) by markers as described herein—such as by evaluating if $PD-1^+$ T cells or PD-1 levels are decreased or if levels of granzyme B or IFN γ production by $CD8^+$ T cells is restored or increased.

Identifying suitable therapeutic dosage of sorafenib is known in the art. For example, a common dosage is 400 mg orally. It is routinely given to patients 400 mg PO BID—meaning per orally bis in die (i.e., twice a day). Range of doses for anti-PD-1 can be tested, including for safety/lack of toxicity by well-known techniques. In one embodiment, the dosage may be varied from 300-500 mg orally or from 350 to 450 mg orally PO BID.

In one embodiment, treatment with a first dosage of sorafenib is carried out from 1 to 20 weeks or as deemed appropriate by a treating physician. In various embodiments it may be carried out for 2 to 10 weeks. In one embodiment, treatment with a second dose of sorafenib and PD-1 inhibitor may be carried out for as long as required.

In one embodiment, a method is provided whereby currently used doses of sorafenib may be decreased by administration of PD-1 inhibitor. Thus, for example, administration of a PD-1 antibody may allow lowering the therapeutically required dosage of sorafenib—thus alleviating toxicity issues. In one embodiment, the dosage of sorafenib may be reduced by 5 to 99% and all percentages therebetween.

In one embodiment, the method comprises administering a lower doses of TK inhibitor (such as sorafenib) than is currently administered and then contemporaneously or subsequently administering a PD-1 inhibitor.

In embodiments, the method of the present disclosure uses pharmaceutical compositions comprising a TK inhibitor and/or PD-1 inhibitor in pharmaceutically acceptable carriers. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil, olive oil, gel (e.g., hydrogel), and the like. Saline is a preferred carrier when the pharmaceutical composition is administered intravenously. Saline solutions and aqueous dextrose and glycerol solutions can also be employed as liquid carriers, particularly for injectable solutions.

In one embodiment, the method comprises a prognostic method for determining if the outcome of continued sorafenib therapy is likely to be favorable. The method comprises administering sorafenib to an individual with HCC and then after a suitable period of treatment (such as from 1-20 weeks and all weeks therebetween), evaluating for PD-1 levels on $CD4^+$ or $CD8^+$ T cells, wherein reduced PD-1 levels are indicative of a favorable outcome. The favorable outcome may be longer survival time compared to individuals who do not exhibit lowered PD-1 levels. Based on lowered PD-1 levels, clinicians may design appropriate treatment strategies for patients—including continued treatment with sorafenib, with or without PD-1 antibody treatment, or adjusting the level of sorafenib (such as lowering the dosage) with or without PD-1 antibody The individual may be a human or a non-human animal such as a woodchuck or any other animal including domestic animals. The compositions of the present disclosure may be administered using any conventional route including—intravenous, intramuscular, intraperitoneal, intratumoral, and via the mucosal route, or topical route.

In one aspect, the disclosure provides a composition comprising a sub-therapeutically effective dosage of sorafenib and a PD-1 antibody in a pharmaceutically acceptable carrier, wherein the sub-therapeutically effective dosage is from 100 to 250 or 100-300 mg/2× per day. The term "sub-therapeutically effective" as used herein means a dose of sorafenib that when used alone will not be considered to be therapeutically effect. For example, a therapeutically effective dose of sorafenib in human adults is considered to be about 400 mg/2× per day.

In one aspect, the disclosure also provides a kit useful for the treatment of HCC. In one embodiment, the kit comprises one or multiple doses of a TK inhibitor, one or multiple doses of a PD-1 inhibitor, instructions on administration regimens, timing and frequency, and optionally devices for administration of the components. In one embodiment, the TK inhibitor is sorafenib and the PD-1 inhibitor is a PD-1 antibody.

In one embodiment is provided a kit comprising one or more of the following: a supply of a first dosage of a TK inhibitor such as sorafenib, a supply of a combination of second dosage of the TK inhibitor such as sorafenib and a PD-1 inhibitor, wherein the second dosage of TK inhibitor such as sorafenib is lower than the first dosage, and instructions for use. The combination of the second dosage of sorafenib and PD-1 inhibitor may be in the same composition or different compositions. For example, each vial or container may contain only one administration dose. The supply of TK inhibitor and PD-1 inhibitor may be present in one or multiple containers or vials. Optionally, the kit may also contain compositions for detection of PD-1 levels on $CD4^+$ and/or $CD8^+$ T cells.

In one embodiment is provided a kit comprising one or more of the following: a supply of a first dosage of sorafenib which will provide a dosage of 400 mg twice a day to an individual, a supply of a combination second dosage of sorafenib which is lower than the first dosage and PD-1 antibody, and instructions for use. The combination second dosage of sorafenib and PD-1 antibody may be the same formulation or separate formulations. The supply of the first dosage of sorafenib and the second dosage of sorafenib may be present in one or multiple containers or vials. For example, each vial or container may contain only one administration dose. Optionally, the kit may also contain compositions for detecting PD-1 levels on $CD4^+$ and/or $CD8^+$ T cells, In one embodiment is provided kits comprising a supply for a first dosage of sorafenib which is 400 mg/dose given twice a day (or any other dosage disclosed herein) and a supply of a second dosage of sorafenib which is lower than the first dosage (such as 100-300 mg twice a day), and a supply of anti-PD-1. The supply for each may be a plurality of vials, with each vial containing a single administration dose. Optionally, detection tools for determining levels of PD-1 on T cells are also provided. Optionally, instructions for the administration of the therapeutics and determination of PD-1 status are also provided.

The following examples are provided to illustrate the disclosure. These examples are not intended to be limiting.

Example 1

In this study, we examined Tregs and immunosuppressive factors as they have been implicated to be independent prognostic factors regardless of the etiology of HCC. Although molecules such as CD25, CTLA-4, CD62L and CD127 are differentially expressed on Tregs, they are also expressed during chronic T cell activation or differentiation, and therefore these markers may not adequately discriminate Tregs with high suppressive potential from recently activated T cells. We elected to evaluate GARP expression in order to distinguish highly suppressive $Foxp3^+$ Tregs in HCC patients from $Foxp3^+$ T cells that do not exert suppressive function. We also studied the prevalence of MDSC cell subset in HCC patients, and compared T cell PD-1 expression levels in HCC patients and healthy controls in order to elucidate the potential role of T cell exhaustion in the immune profile of advanced stage HCC.

This represents the first study that has determined whether targeted depletion of immunosuppressive cells in advanced HCC has the potential to restore endogenous anti-tumor T cell function.

Materials and Methods

Blood Samples

Heparinized peripheral blood samples were obtained from HCC patients through Data Bank and Biorepository at RPCI and from healthy donors after obtaining informed consent. Clinical therapy and baseline demographic data were recorded. Clinical characteristics were collected by chart review (Table 1) and merged with immune results that were analyzed in blinded fashion. PBMC were isolated by Ficoll-Paque™ PLUS density gradient centrifugation of blood samples (GE Healthcare) as described in Suresh et al.

Tregs

FACS analysis was performed to measure peripheral blood Treg frequency using APC-H7 anti-CD3, V450 anti-CD4, PE anti-CD127, PE-Cy5 anti-CTLA-4 (BD Biosciences) and PE-Cy7 anti-PD-1, Alexa488 anti-Foxp3 (Biolegend). Detection of surface GARP levels was achieved by using mouse anti-human GARP (Enzo Life Sciences) followed by staining with PE $F(ab')_2$ goat anti-mouse IgG (Jackson ImmunoResearch Laboratories). Cells were incubated with normal mouse IgG for 10 min prior to surface and intracellular staining. Intracellular analysis for Foxp3 and CTLA-4 was performed after fixation and permeabilization of cells using intracellular staining kit (eBioscience) according to manufacturer's instructions. All samples were acquired on LSRII flow cytometer (BD Biosciences) and analyzed using Flowjo Model Fit (Tree Star).

MDSC

MDSC in the peripheral blood were detected using FITC anti-CD11b (eBioscience), PE-Cy5 anti-CD33, APC anti-CD14, V450 anti-HLA-DR (BD Biosciences).

Cytokine ELISA

Plasma isolated during PBMC separation was assayed to quantify the level of IFN-γ, IL-10, and TGF-β1 using specific ELISA kits according to the manufacturer's instructions (eBioscience).

Depletion of Suppressor Cells from PBMC

HCC patient PBMC depleted of $GARP^+$, $CTLA-4^+$, and $PD-1^+$ T cells (gated on the $CD3^+CD4^+$ T cells) were obtained by cell sorting using a FACSAria. $CD33^+$ MDSC were eliminated after gating on $HLA-DR^-CD14^-$ cells. PBMCs with and without the depleted suppressor cells were used to measure effector T cell proliferation and cytokine production when stimulated with PHA or anti-CD3/anti-CD28 in vitro as described below.

Lymphocyte Proliferation Assay

Carboxyfluorescein succinimidyl ester (CFSE) staining of PBMC was performed according to the manufacturer's instructions (Invitrogen). Briefly, $1\times10^7$ PBMCs were incubated in HBSS containing 2 mM CSFE for 10 min at 37° C. and then washed three times with RPMI medium containing 10% human AB serum. Labeled cells ($5\times10^4$ cells/well) were incubated in the presence or absence of 5 µg/ml PHA (Sigma) or 1 µg/ml anti-CD3 antibody and 0.5 µg/ml anti-CD28 antibody (eBioscience) in a 96 well flat bottom plate. After four days of stimulation, harvested cells were stained with APC-H7 anti-CD3, V450 anti-CD4 and V500 anti-CD8.

Intracellular Cytokine-Staining Assay

Four hours prior to harvesting PBMCs treated with PHA or anti-CD3/anti-CD28, PMA (20 ng/ml), 1 µl of 1 mM ionomycin/ml (Sigma) and 1 µg/ml of monensin (BD Biosciences) were added to the culture. Cells were washed and stained with APC-H7 anti-CD3 for 30 min at 4° C. After fixation and permeabilization, intracellular staining was performed using V450 anti-CD4, V500 anti-CD8, PE anti-IFN-γ, PE anti-granzyme B, PE isotype control and Alexa700 anti-Foxp3 (eBioscience).

Statistical Analysis

Our primary objective was to compare immunophenotypes in HCC patients (n=23) and healthy controls (n=20). For each of 29 possible outcomes, the null hypothesis of no difference in the outcome distribution between the two groups was assessed using an Exact Wilcoxon Rank Sum (Mann-Whitney U) test. Per-comparison two-sided p-values less than 0.05 were considered statistically significant. With 23 patients in each group, similarly conducted experiments have 80% power to detect a minimum difference in mean expression of 0.9 standard deviations. Tests for functional responses were done in HCC patients (n=8) and healthy controls (n=8). Patients were selected on the basis of either elevated levels of Tregs/MDSC or low levels of the same. Tests of this nature have 80% power to detect a minimum difference of 1.5 standard deviations.

Post-depleted HCC and healthy control samples were also compared using the Exact Wilcoxon Rank Sum (Mann-Whitney U) test. Matched pre-depleted and post-depleted samples within the HCC patients were compared using the Wilcoxon Signed Rank Test.

Given the number of comparisons conducted, we also considered a correction for multiple testing. Methods developed by Hochberg (Hochberg Y. A Sharper Bonferroni Procedure for Multiple Tests of Significance. Biometrika Trust; 1988. p. 800-2 were used to identify outcome differences in the HCC and control subjects that maintained a 0.05 family-wise Type I error rate. Based on the 29 tests considered, this method identified 15 comparisons with per-comparison p-values less than 0.0027 as being interesting.

Plasmacytoid DC (pDC)

Circulating pDC were identified by the following staining panel: V450 anti-HLA-DR, APC anti-CD86, PE anti-CD80, PE anti-CD83 (BD Biosciences), FITC anti-CD11c and PE-Cy7 anti-CD123 (eBioscience). The PE-Cy5 conjugated lineage markers for CD3, CD14, CD19, and CD56 were used to exclude T cells, monocytes, B cells, and NK cells.

RNA Extraction and cDNA Synthesis

RNA extraction and cDNA synthesis was performed using RNeasy Protect Mini Kit (Qiagen) and Omni script reverse transcription kit (Qiagen) as described in Suresh et al.

Quantitative PCR q-PCR was performed on Bio-Rad CFX96™ Real-Time system using gene specific TaqMan probes and primers for Foxp3 (Hs01085835), CTLA-4 (Hs034418), PD-1 (Hs01550089), GARP (Hs00194136) and endogenous control human GAPDH (Applied Biosystems) as described in Suresh et al.

Results

Patients

Clinical characteristics of HCC patients are summarized in Table 1. At the time of this report 17/23 HCC patients have died and median survival for these patients is 7 months (range 1-21 months). For the surviving 6 patients, median follow up from time of PBMC collection is 14 months (range 12-25 months). All 23 HCC patients analyzed in this study had locally advanced or metastatic disease and none had early stage surgically resectable or transplantable disease.

TABLE 1

| Patient characteristics | HCC (n = 23) | Normal Healthy (n = 20) |
|---|---|---|
| Gender (M:F) | 16:7 | 10:10 |
| Median age (yrs) | 64 (40-82) | |
| Child Pugh Class Liver function | A = 16<br>B = 7<br>C = 0 | — |
| BCLC class | A = 0<br>B = 21<br>C = 2<br>D = 0 | — |
| Etiology of liver disease | Hepatitis B = 1<br>Hepatitis C = 13<br>Hepatitis B and C = 1<br>Alcohol = 2<br>No known risk factor = 6 | — |
| Prior therapies (some patients had more than one therapy hence numbers ≠ 23) | None = 10<br>Locoregional = 8<br>Chemotherapy or biologic therapy = 7<br>Liver resection = 4 | — |

For the stimulation assays 8 patients were chosen. Of those patients 5 are alive, median follow up time is 15 months (range 12-25 months) and of the 3 patients who have died, median survival was 7 months (range 2-10 months). The patients had BCLC class B (n = 7) or C (n = 1) liver function and Child Pugh class A (n = 6) or class B (n = 2) liver function. The etiology of cirrhosis was chronic hepatitis C (n = 4) and neither hepatitis HBV or HCV (n = 4).

Cirrhosis

By radiographic criteria, 11/23 patients showed no signs of cirrhosis and 5 of them also had prior liver resection that confirmed this. Ten of these 11 patients also had Child Pugh liver cirrhosis score Class A, while one patient was a class B, confirming the limited sensitivity of radiographic methods to assess degree and or presence of cirrhosis. Of the remaining 12/23 patients had some evidence radiographically (CT, MRI, USG or more than one) of cirrhosis and none were deemed as surgical candidates, even though 5 of them had Child Pugh Class A or good liver function.

Tregs in Advanced HCC Exhibit a Highly Immunosuppressive Phenotype

Figure 6:
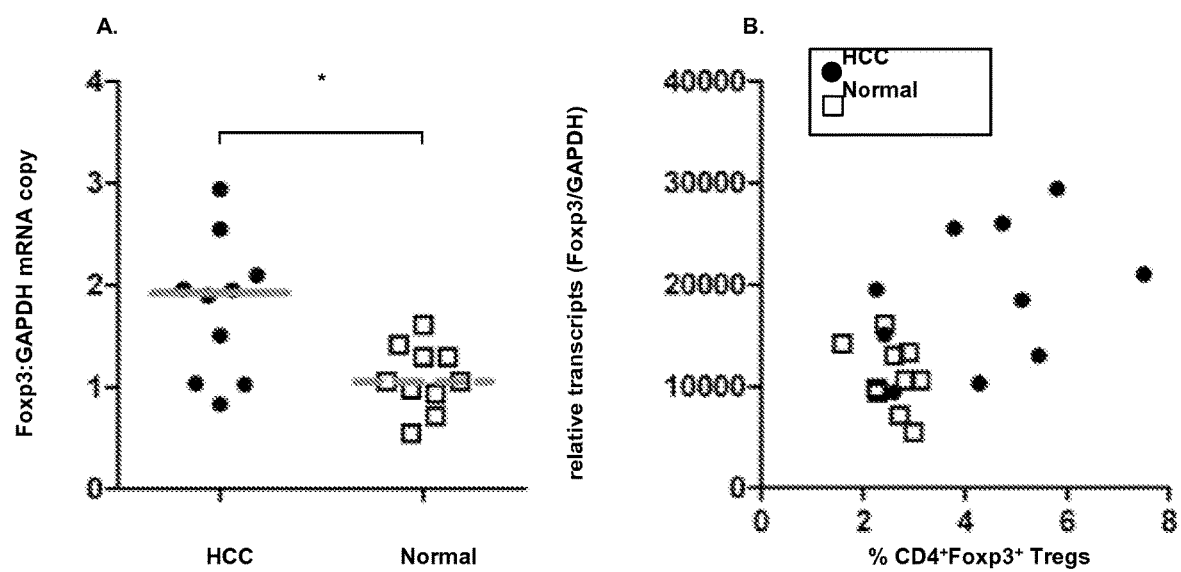
FIGS. 6A-6B. Foxp3 gene expression from PBMCs of HCC patients.
Figure 7:
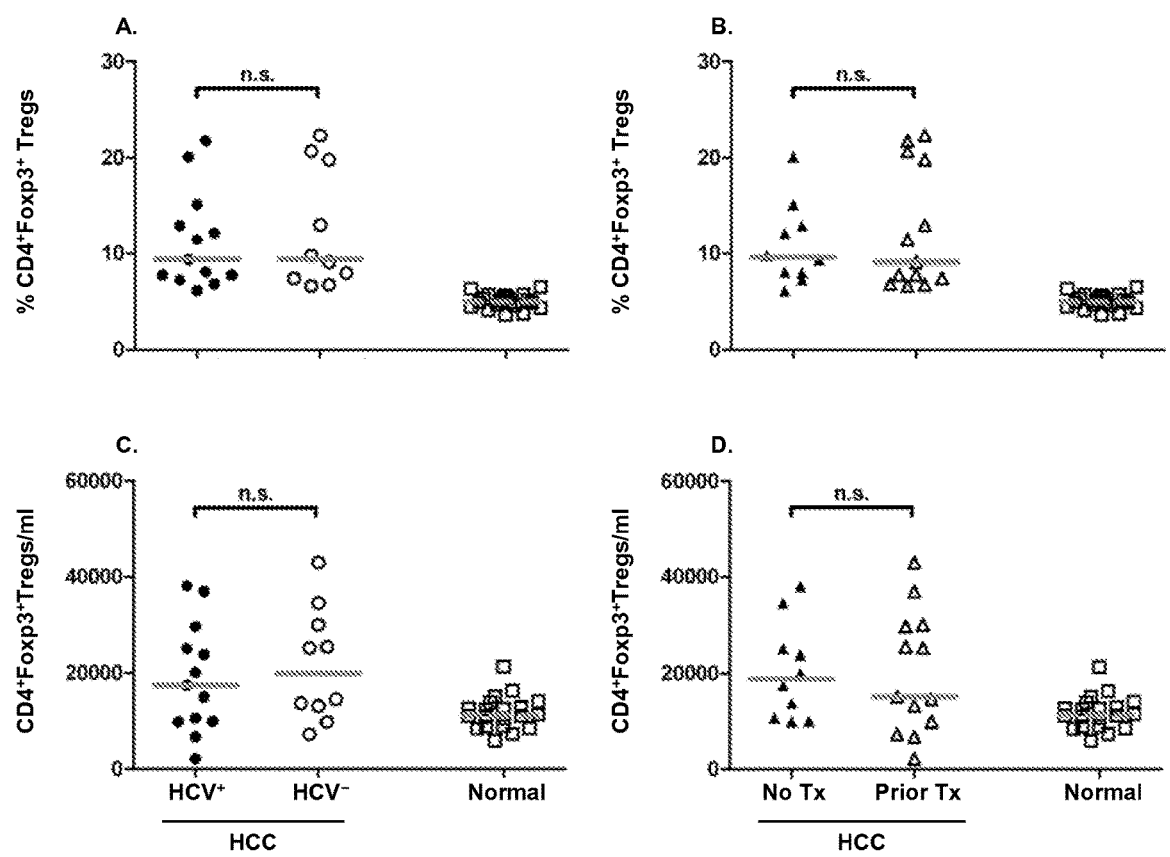
FIGS. 7A-7D. Impact of chronic viral infection or pretreatment of HCC patients on Tregs. HCC patients were stratified based on HCV⁺/HCV- or prior treatment/treatment naïve and (FIG. 7A, FIG. 7B) frequency as well as (FIG. 7C, FIG. 7D) absolute number of CD4⁺Foxp3⁺ Tregs in the peripheral blood of HCC patients was compared. Each symbol represents an individual HCC patient (●) or normal healthy subjects (□). Lines represent median values for the group.
Figure 8:
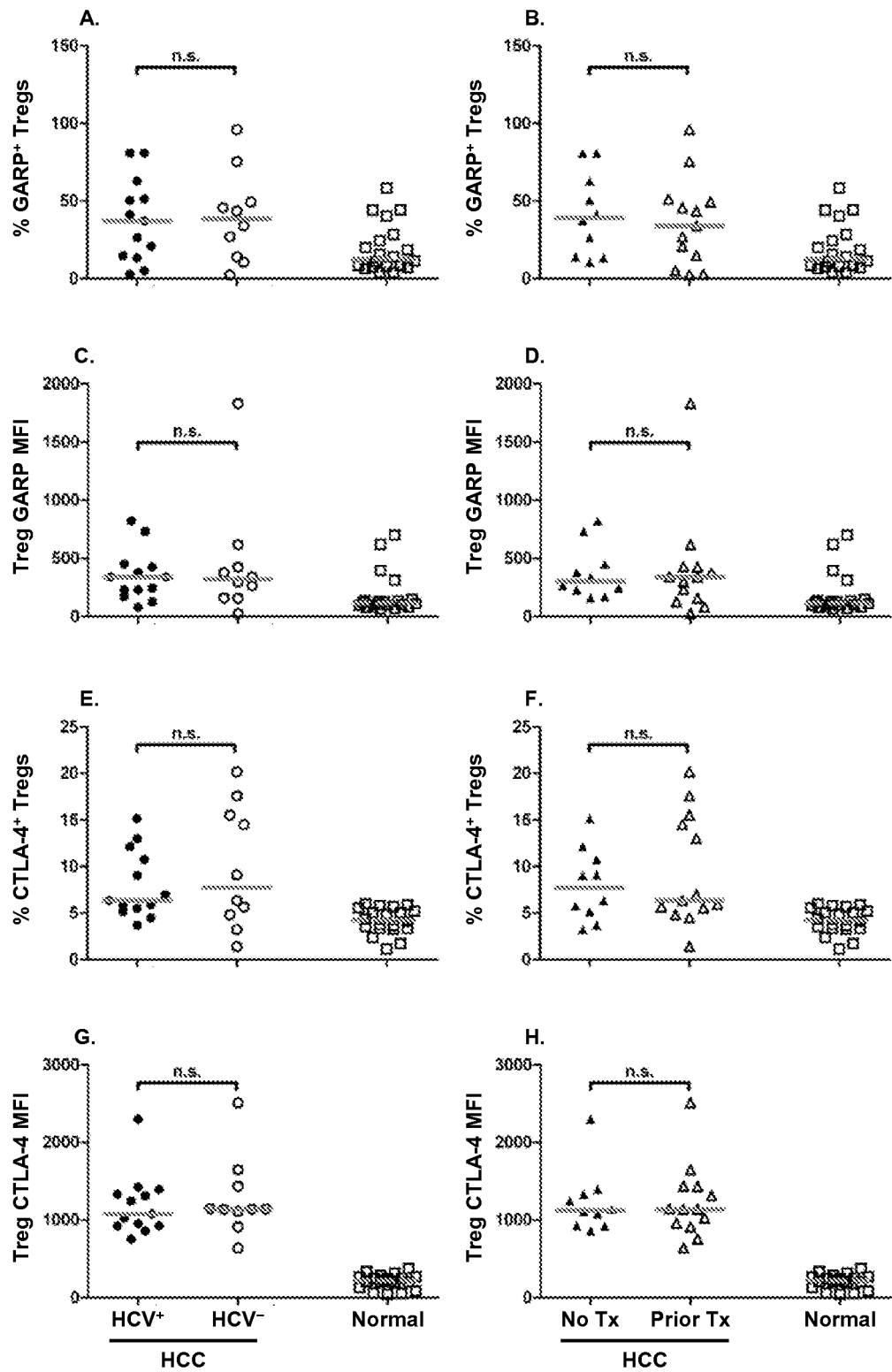
FIGS. 8A-8H. Effect of chronic viral infection or pretreatment of HCC patients on GARP and CTL-A4 expression. HCC patients were segregated based on HCV⁺/HCV- or prior treatment/treatment naïve and (FIG. 8A, FIG. 8B) frequency of GARP-expressing CD4⁺Foxp3⁺ Tregs or (FIG. 8C, FIG. 8D) GARP expression levels on CD4⁺Foxp3⁺ Tregs measured by mean fluorescent intensity was compared.
Figure 9:
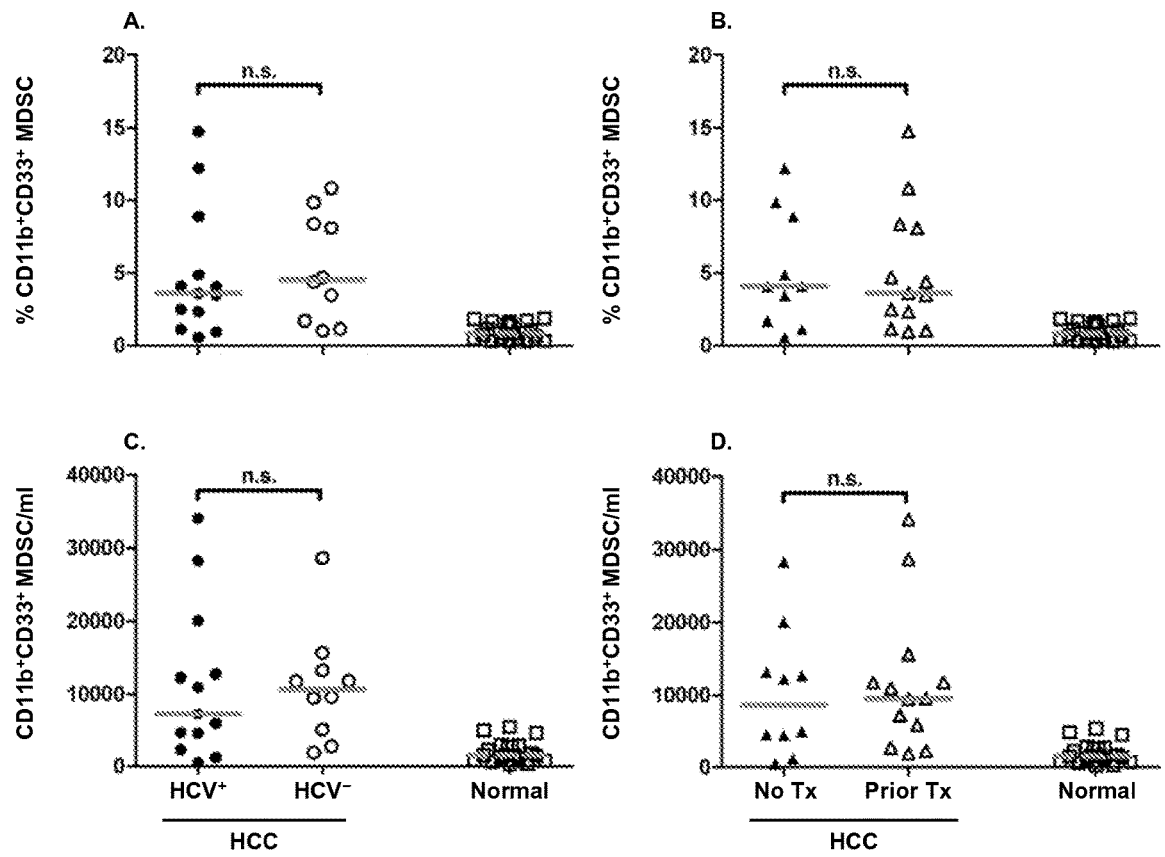
FIGS. 9A-9D.

Using the baseline parameters for Tregs that other investigators have established, we also begin our study by measuring the frequency of $CD3^+CD4^+Foxp3^+$ Tregs. These cells were additionally identified by exclusion of CD127 expression. Representative staining and gating of $CD4^+$ $Foxp3^+$ Tregs from one HCC patient (FIG. 1A) and one normal donor (FIG. 1B) are shown; the Tregs were present at higher frequencies in HCC patients compared to normal controls (HCC: 9.4%±5.4 vs. normal: 5.0%±0.78; P=0.001) (FIG. 1C). In addition, the absolute number of $Foxp3^+$ T cells in the peripheral blood was also greater in the HCC patients compared to controls (HCC: 17,440 cells/ml±11,343 vs. normal: 11,282±3,486 cells/ml; P=0.015) (FIG. 1D). The ratio of Foxp3 mRNA copy number was significantly increased in HCC patients as compared to controls (FIG. 6A). A significant correlation was seen between Foxp3 gene expression and percentage of $CD4^+Foxp3^+$ T cells (FIG. 6B), confirming that the two assays measure the same cell population. Comparison of Treg frequencies or absolute number after stratification of patients based on HCV status (FIG. 7A, C) or having received prior treatment (FIG. 7B, FIG. 7D) did not influence the level of Treg accumulation in HCC patients.

We expanded our analysis of $Foxp3^+$ Tregs to include measurement of GARP (FIG. 1E, FIG. 1F) and CTLA-4 (FIG. 1I, FIG. 1J) to determine whether these cells in HCC patients exhibited a highly immunosuppressive phenotype. Evaluation of GARP and CTLA-4 expression on Tregs in advanced HCC has not been previously reported and therefore the analysis of these two markers of highly immunosuppressive Tregs is critical to understanding the nature of Treg-mediated immune suppression in HCC patients The frequency of $GARP^+Foxp3^+$ Tregs was significantly higher in HCC patients than in controls (HCC: 37.1%±27.1 vs. normal: 12.5%±15.89; P=0.01) (FIG. 1G). The level of GARP expression was also elevated on $Foxp3^+$ Tregs of HCC patients as compared to controls (HCC: 341±368 MFI vs. normal: 116±181 MFI; P=0.001) (FIG. 1H). Neither chronic viral infection nor prior treatment of HCC patients had any impact on the profiles of GARP expression in patients (FIG. 8A-8D).

The frequency of $Foxp3^+$ Tregs that expressed intracellular CTLA-4 was also significantly greater in HCC patients compared to controls (HCC: 6.4%±5.0 vs. normal: 4.2%±1.4; P=0.001) (FIG. 1K). In addition, CTLA-4 expression levels were also significantly higher on Tregs from HCC patients as compared to controls (HCC: 1,137±440 MFI vs. normal: 218±94.4 MFI; P=0.001) (FIG. 1L). Neither the frequency of $CTLA-4^+$ T cells nor the CTLA-4 expression levels were influenced by chronic viral infection or prior treatment (FIG. 8E-8H). The presence of $GARP^+CTLA-4^+$ Tregs represents the first identification of a highly immunosuppressive Treg population in advanced HCC patients and that these cells may pose a significant impediment to the efficacy of anti-tumor responses elicited by immunotherapeutic or cancer vaccine approaches.

Elevated Numbers of MDSC in HCC Patients

Figure 2:
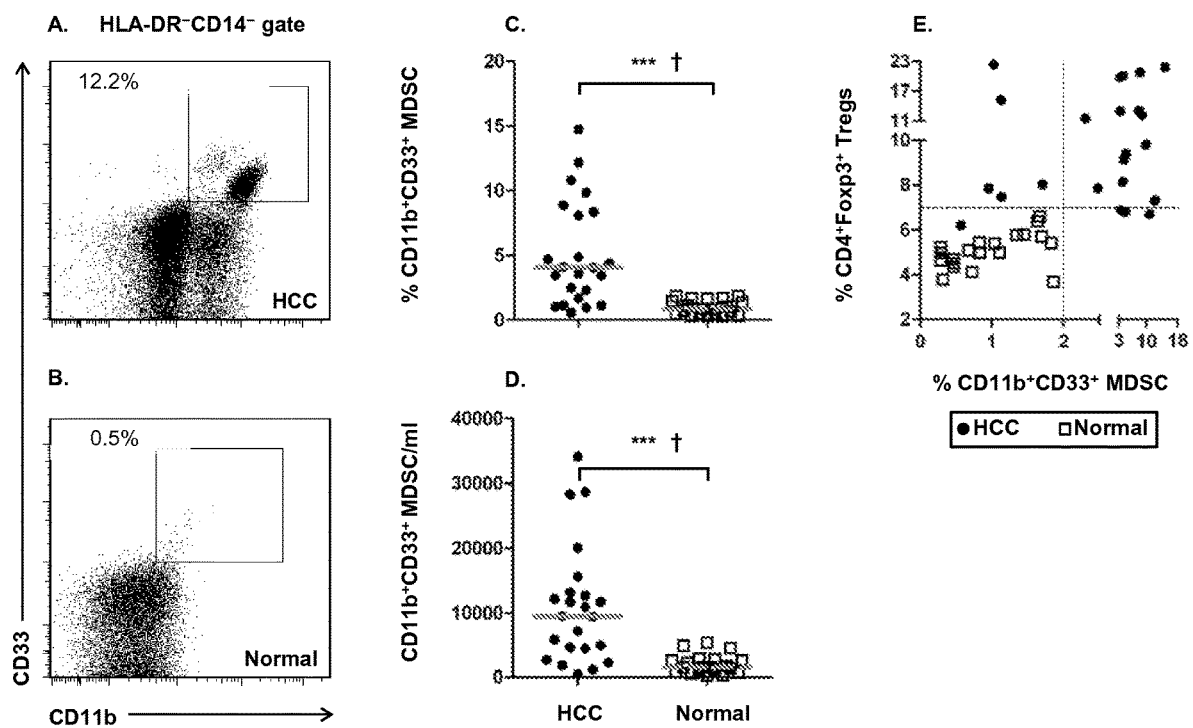
FIG. 2A-2E. Accumulation of MDSCs in HCC patients.

Just as GARP and CTLA-4 have been understudied in advanced HCC, neither have MDSC been evaluated in this patient population despite their importance as an immunosuppressive cell in many cancers. Due to the interconnectedness of MDSC and Treg generation during malignant progression, we measured the frequency of $CD14^-HLA-DR^-CD11b^+CD33^+$ MDSC in each HCC patient for which we measured Treg frequency. Representative MDSC staining patterns from one HCC patient and one normal control are provided in FIGS. 2A and 2B. In conjunction with the elevated Tregs levels, the frequency (FIG. 2C) and absolute number of circulating MDSC (FIG. 2D) was significantly elevated in HCC patients. Additionally, the percentage of MDSC demonstrated excellent correlation with percentage of circulating Tregs (FIG. 2E). HCV infection or prior treatment did not impact MDSC frequency in HCC patients (FIG. 9A-9D). This data formally demonstrates the utility of measuring Tregs and MDSC in the same patient, as 14/23 HCC patients exhibited elevated levels of both immunosuppressive cell types. Thus, the interplay between MDSC and Tregs is likely instrumental in the establishment of the adverse immunosuppressive network in advanced HCC.

Figure 10:
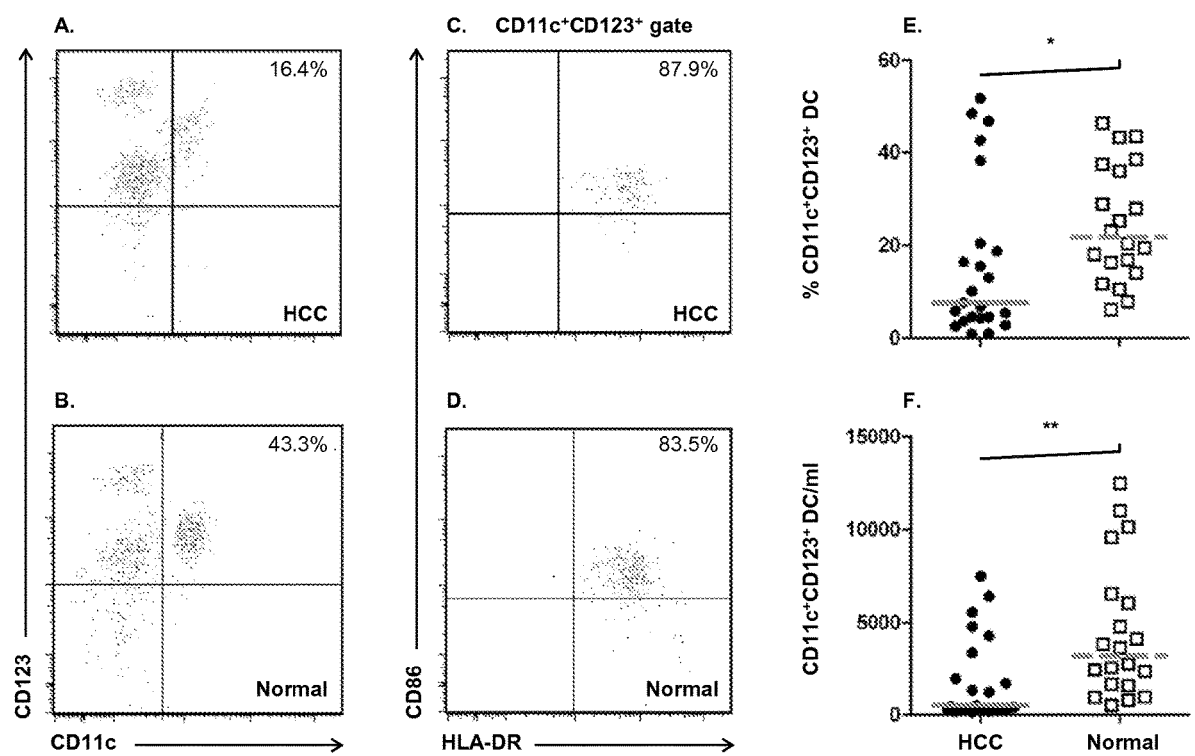
FIGS. 10A-10F. Plasmacytoid dendritic cells in HCC patients.
Figure 11:
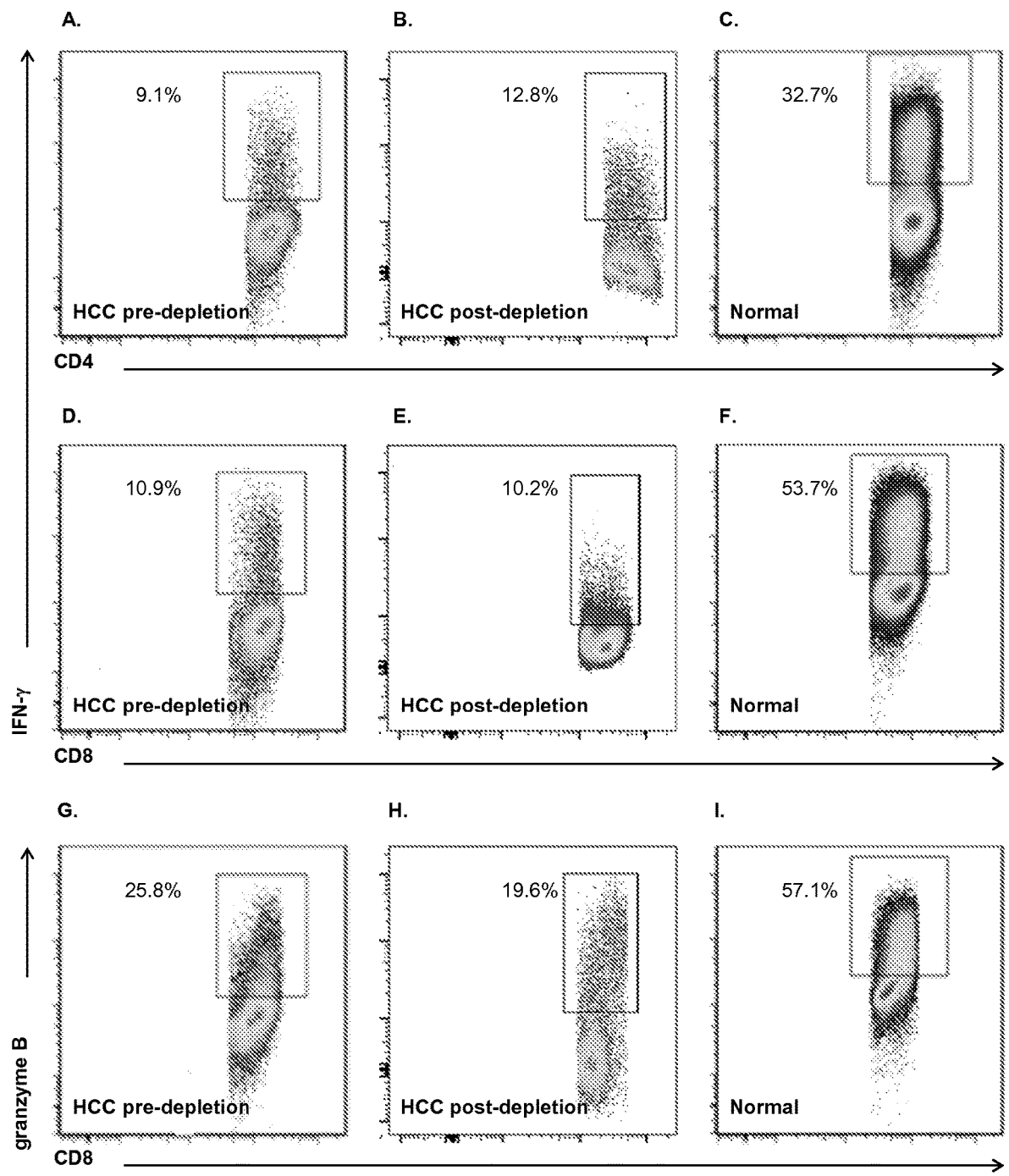
FIGS. 11A-11I. Intracellular cytokine expression from in vitro stimulated T cells. Representative staining pattern for IFN-g in (FIGS. 11A-11C) CD4⁺ and (FIGS. 11D-11F) CD8⁺ T cells from one HCC patient pre-depletion and post-depletion of suppressor cells compared to normal control.

The accumulation of MDSC does not comprise the full impact of all myeloid cells in advanced HCC, as $CD11c^+CD123^+$ pDC (FIG. 10A-10D) were also reduced in HCC patients compared to normal when measured by frequency (FIG. 10E) or absolute number (FIG. 10F).

Elevated Levels of Immunosuppressive Cytokines in HCC Patients

Figure 3:
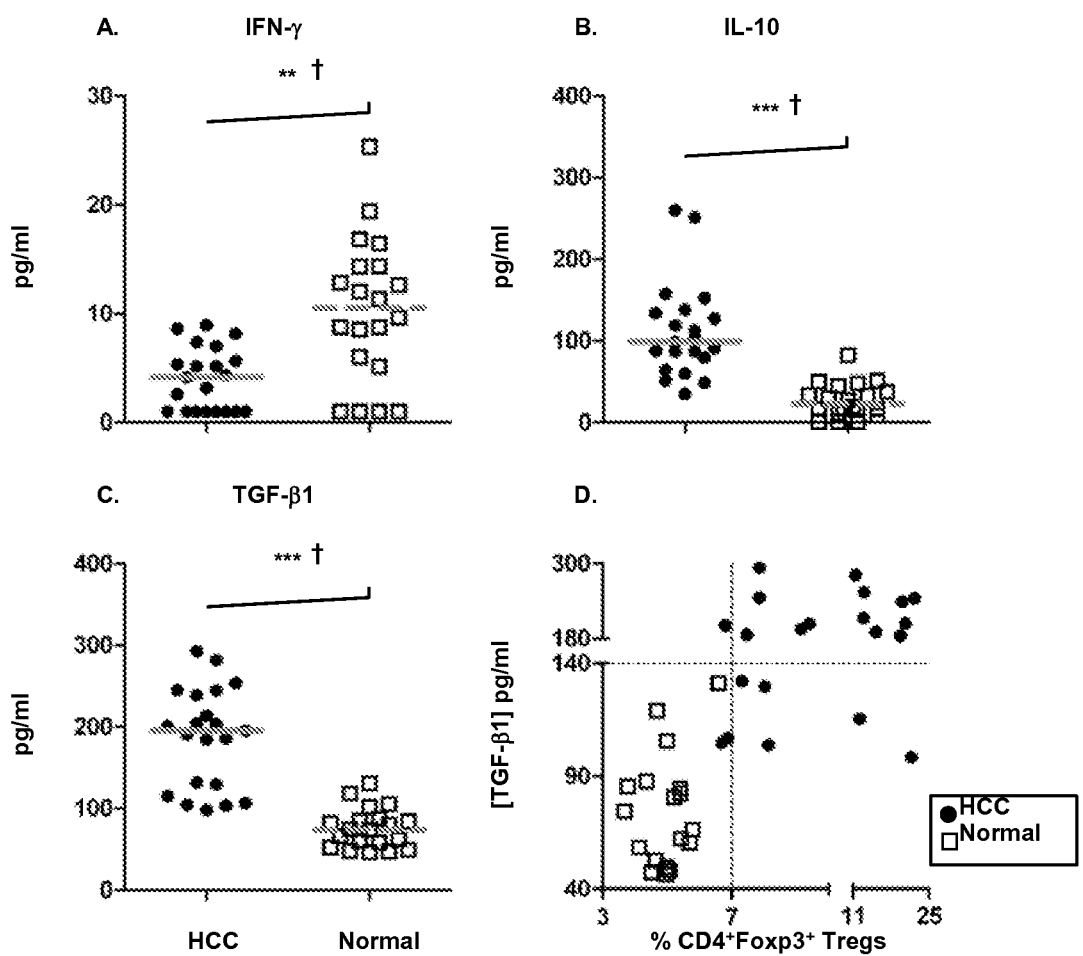
FIGS. 3A-3D. Elevated levels of immunosuppressive cytokines in HCC patients.

The phenotype of augmented immunosuppression in HCC patients is additionally reflected by the diminished levels of plasma IFN-γ (FIG. 3A), a potent anti-tumor cytokine whose levels can be downregulated by the presence of Tregs. In addition to the low levels of IFN-γ, a significant increase in the levels of two Treg-generated immunosuppressive cytokines, IL-10 and TGF-β1 was found in HCC patients (FIG. 3B, FIG. 3C). The elevated levels of $Foxp3^+$ Tregs in HCC patients are also associated with corresponding high plasma levels of TGF-β1 (FIG. 3D). Therefore, our results demonstrate that the cytokine milieu in which the HCC disease progresses is skewed toward an immunosuppressive phenotype and will likely adversely impact the effector function of anti-tumor immune responses while simultaneously stimulating tumor-promoting immune responses.

HCC Patients have Increased PD-1 Expression on Circulating $CD4^+$ T Cells

We examined whether $PD-1^+$ exhausted $CD4^+$ T cells are also present as an additional indicator of diminished effector function. Both the frequency of $PD-1^+CD4^+$ T cells (HCC: 19.0%±11.3 vs. normal: 8.7%±4.8; P=0.001) (FIG. 4A) and PD-1 expression levels (HCC: 139±72 MFI vs. normal: 46 MFI±31; P=0.001) (FIG. 4B) in HCC patients was significantly higher than in healthy donors. Thus, the accumulation of exhausted $CD4^+$ T cells in HCC patients is another harbinger of immune dysregulation that must be overcome in order to elicit efficacious anti-tumor immune responses.

Impaired T Cell Proliferation in HCC Patients

The presence of an extensive immunosuppressive network undermines endogenous anti-tumor immunity by impairment of T cell function. Given the presence of exhausted T cells, we evaluated whether T cell proliferation and cytokine production were also dysregulated. $CD4^+$ and $CD8^+$ T cell effector function was measured with two polyclonal stimuli, the potent mitogen PHA and anti-CD3/anti-CD28, a surrogate for antigen-specific TCR-mediated stimulation. Further, to ascertain the contribution of Treg, MDSC, and PD-1$^+$ exhausted T cell accumulation on effector T cell function these immunosuppressive cells were depleted, and the function of the remaining effector T cells was analyzed in their absence. We have for the first time directly tested whether targeted depletion of immunosuppressive cells in advanced HCC has the potential to restore endogenous anti-tumor T cell function.

Figure 4:
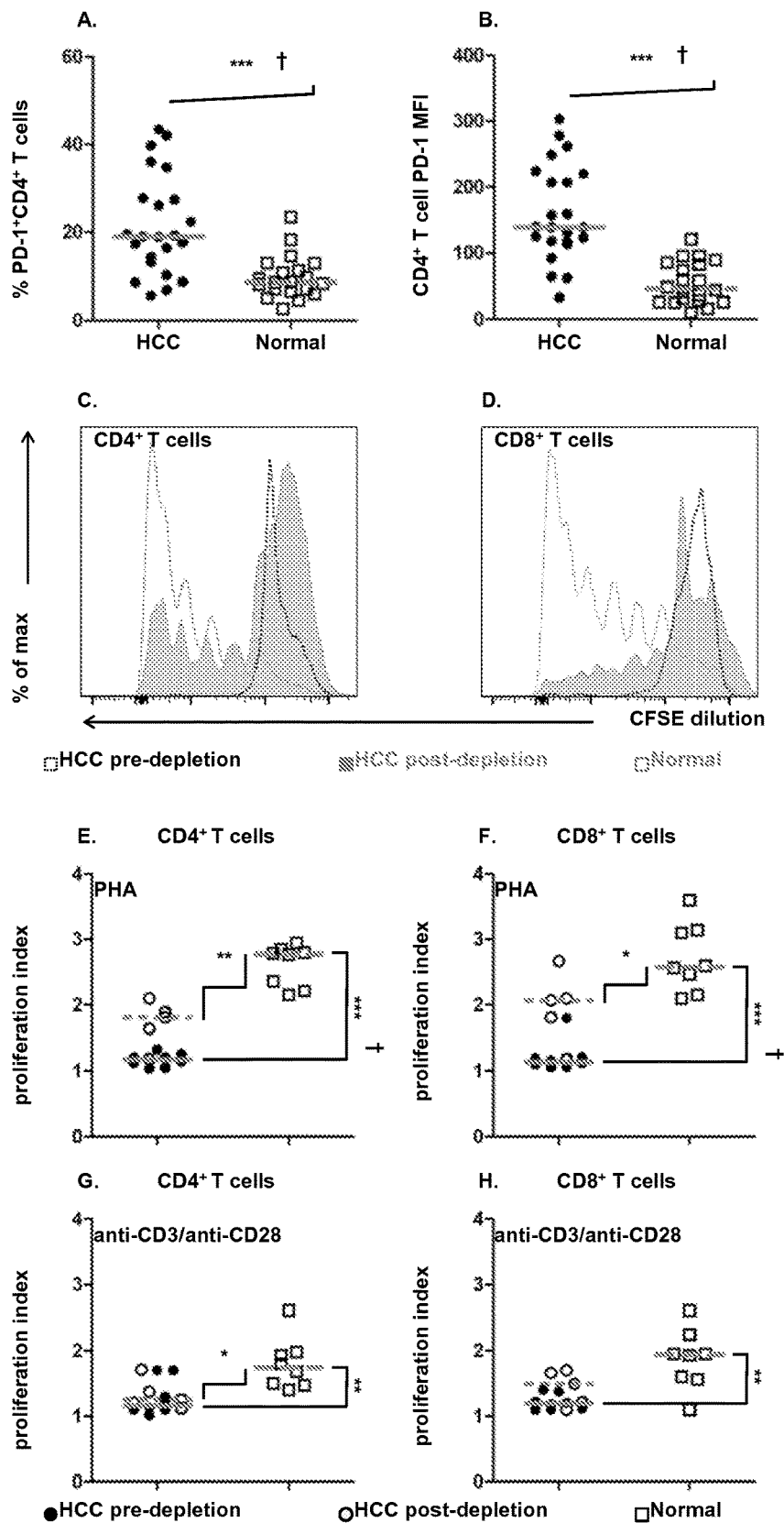
FIGS. 4A-4H. Exhausted T cells from HCC patients exhibit defective proliferation.

Proliferation of CD4$^+$ and CD8$^+$ T cells assessed by CFSE dilution revealed that both subsets from HCC patients exhibited severely impaired responses to PHA stimulation compared to T cells from normal subjects (FIG. 4C, FIG. 4D □ vs □ and FIG. 4E, FIG. 4F ● vs □). Additionally the depletion of the three immunosuppressive cells resulted in only moderate improvement in PHA-mediated T cell proliferation for both CD4$^+$ and CD8$^+$ T cells (FIG. 4C, FIG. 4D ■ and FIG. 4E, FIG. 4F ○ vs ●). Despite the modest improvement in T cell proliferation, Treg, MDSC, and PD-1$^+$ depletion did not restore HCC T cell proliferation that was equivalent to that observed in normal T cells. (FIG. 4E-4H ○ vs □).

Selective Restoration of T Cell Cytokine Production Upon Depletion of Immunosuppressive Cell Subsets We measured IFN-γ and granzyme B production by CD4$^+$ and CD8$^+$ T cells in the presence or absence of Tregs, MDSC, and PD-1$^+$ exhausted T cells (FIG. 1I). IFN-γ producing CD4$^+$ or CD8$^+$ T cells from HCC patients were significantly lower than normal subjects following both PHA and anti-CD3/anti-CD28 stimulation (FIG. 5A-5D ● vs □), once again demonstrating the pervasiveness of immune function dysregulation in advanced HCC patients. Importantly, the frequency of T cells producing this cytokine did not increase appreciably upon depletion of the three immunosuppressive cells (FIG. 5A-5D ○ vs ●). Failure to restore IFN-γ production provides powerful evidence that effector T cells in advanced HCC are unlikely to be able to overcome severe immunodysregulation by targeted depletion of Tregs, PD-1$^+$ T cells and MDSC alone.

Figure 5:
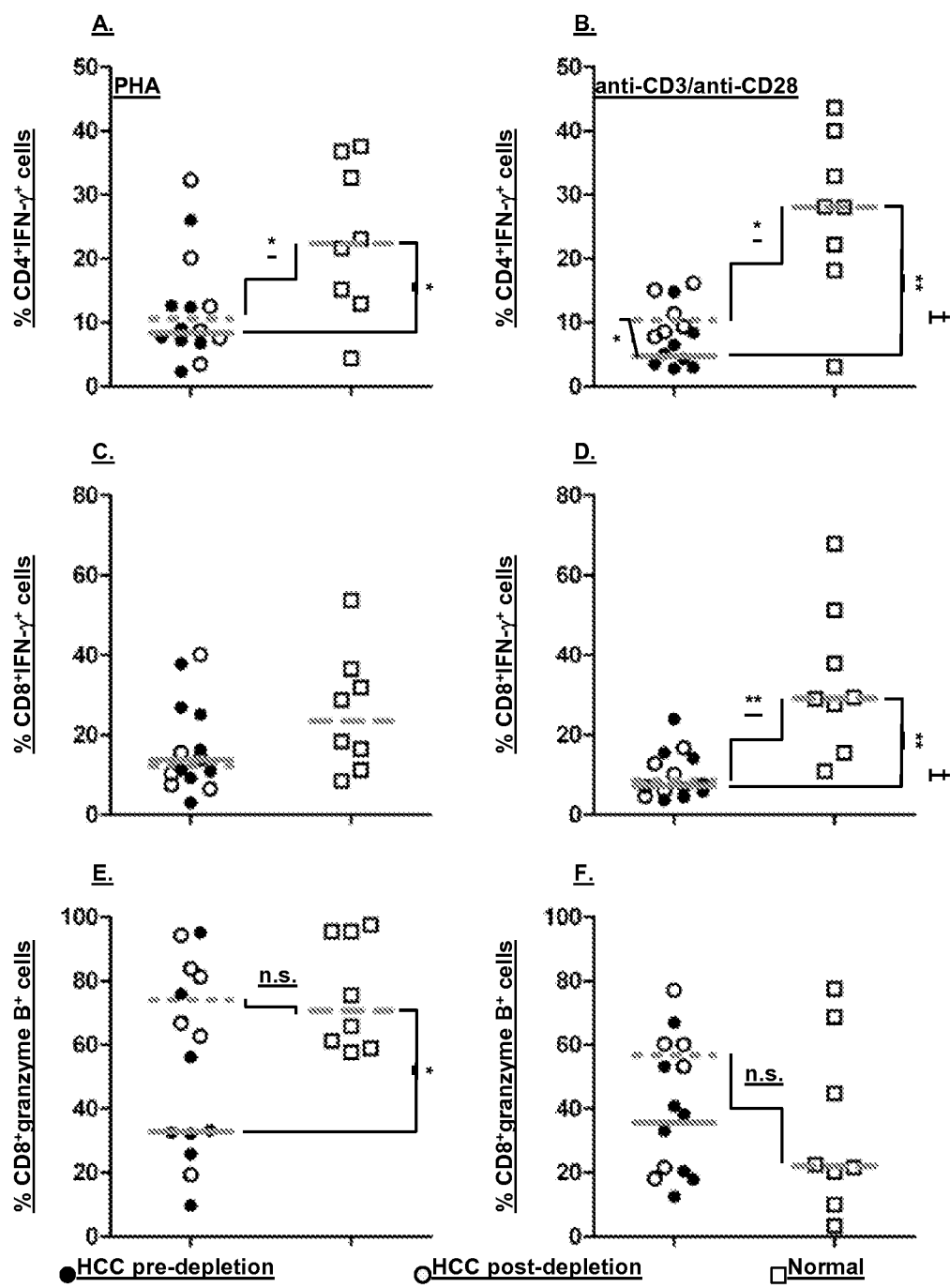
FIGS. 5A-5F. Diminished IFN-γ and granzyme B production by HCC patient T cells. Frequency of (FIG. 5A, FIG. 5B) CD4⁺ T cells and (FIG. 5C, FIG. 5D) CD8⁺ T cells producing IFN-γ upon (FIG. 5A, FIG. 5C) PHA or (FIG. 5B, FIG. 5D) anti-CD3/anti-CD28 stimulation. Frequency of CD8⁺ T cells granzyme B upon (FIG. 5E) PHA or (FIG. 5F) anti-CD3/anti-CD28 stimulation. Each symbol represents an individual HCC patient pre-depletion (●), post-depletion (○), or normal healthy subjects (□); lines represent median values for the group. n.s. not significant, *P<0.05, **P<0.01, Mann-Whitney U test; †P<0.05 Hochberg adjustment for multiple comparison.

Decreased granzyme B production in CD8$^+$ T cells was observed in PHA-stimulated HCC patients compared to normal, but not following anti-CD3/anti-CD28 stimulation (FIG. 5E, FIG. 5F ● vs □). In contrast to IFN-γ production, the frequency of CD8$^+$ T cells producing granzyme B following PHA stimulation was significantly augmented after targeted removal of the three suppressor cells and was equivalent between normal T cells and HCC T cells post-depletion (FIG. 5E ○ vs □). In endometrial cancer patients, an inverse relationship has been shown between the presence of Treg and production of granzyme B expressing CD8$^+$ T cells. In our studies, the depletion of highly suppressive Treg also likely accounts for the increased numbers of granzyme B$^+$CD8$^+$ T cells to levels equivalent to that seen in healthy control subjects. Thus, our findings demonstrate that the restoration of T cell responses after depletion of suppressor cell subsets is restricted and does not ameliorate the entirety of immune dysregulation established in these patients.

In conclusion, we have demonstrated that the augmented numbers of Foxp3$^+$GARP$^+$CTLA-4$^+$ Tregs, MDSC, PD-1$^+$ exhausted T cells, and increased levels of immunosuppressive cytokines represent a plethora of mechanisms by which HCC may foster immune dysregulation. These mediators dampen anti-tumor T cell immunity and may in fact facilitate the progression of HCC. The combined depletion of Tregs, MDSC, and PD-1$^+$ T cells from advanced HCC patients can result in the augmentation of CD8$^+$ T cell granzyme B production and a modest increase in the number of CD4$^+$ T cell IFN-γ producing cells.

Example 2

Figure 12A:
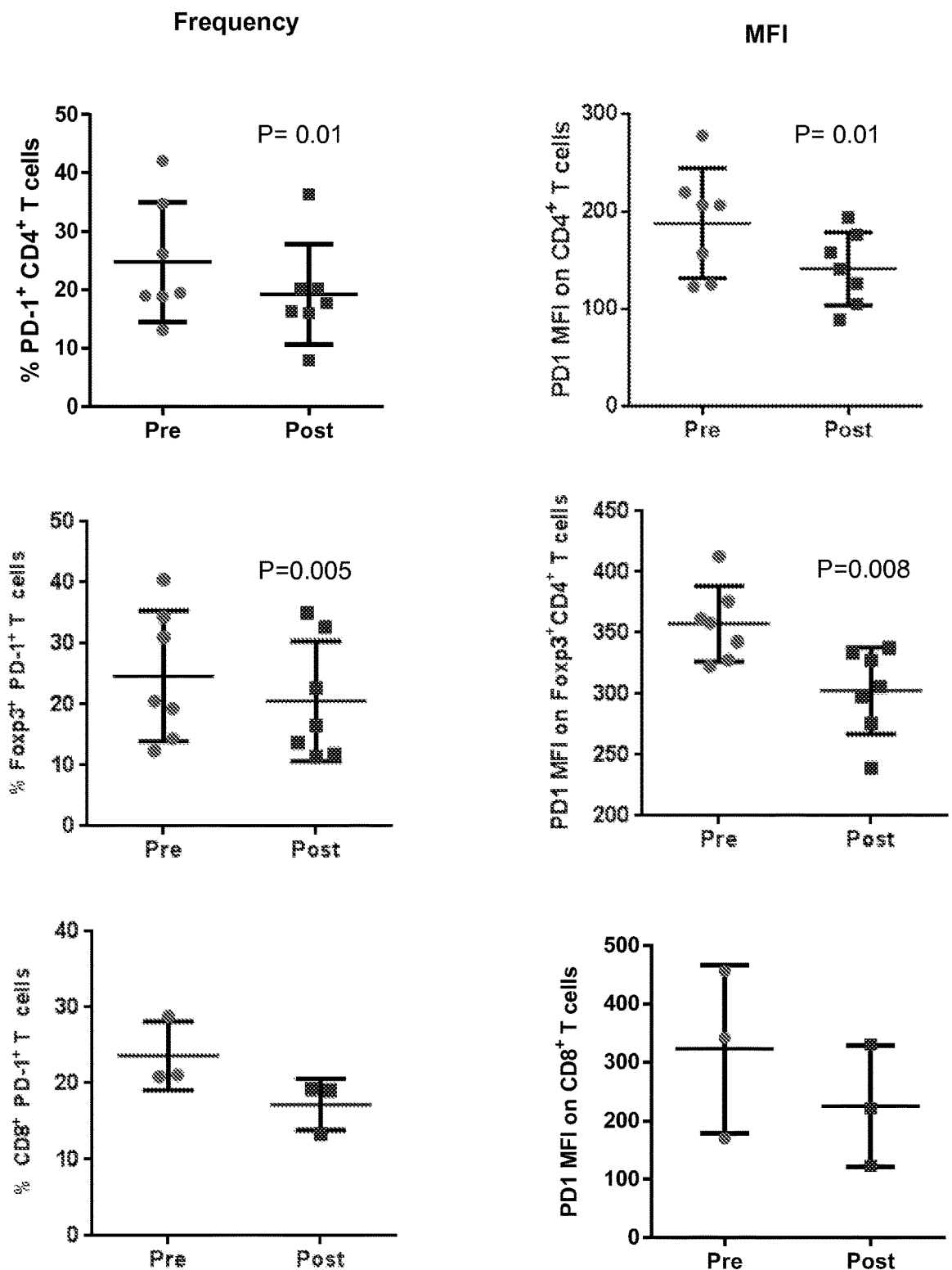
FIGS. 12A and 12B represent results of evaluation for PD-1 levels in HCC patients treated with sorafenib. For each patient, the levels of indicated T cells and levels of PD-1 on the indicated cells were determined before (Pre) and after (Post) a regimen of sorafenib treatment. Based on PD-1 levels, the patients were separated into two groups—one in which PD-1 levels were observed to decrease (FIG. 6A) and one in which the levels did not show any significant decrease (FIG. 6B).
Figure 12B:
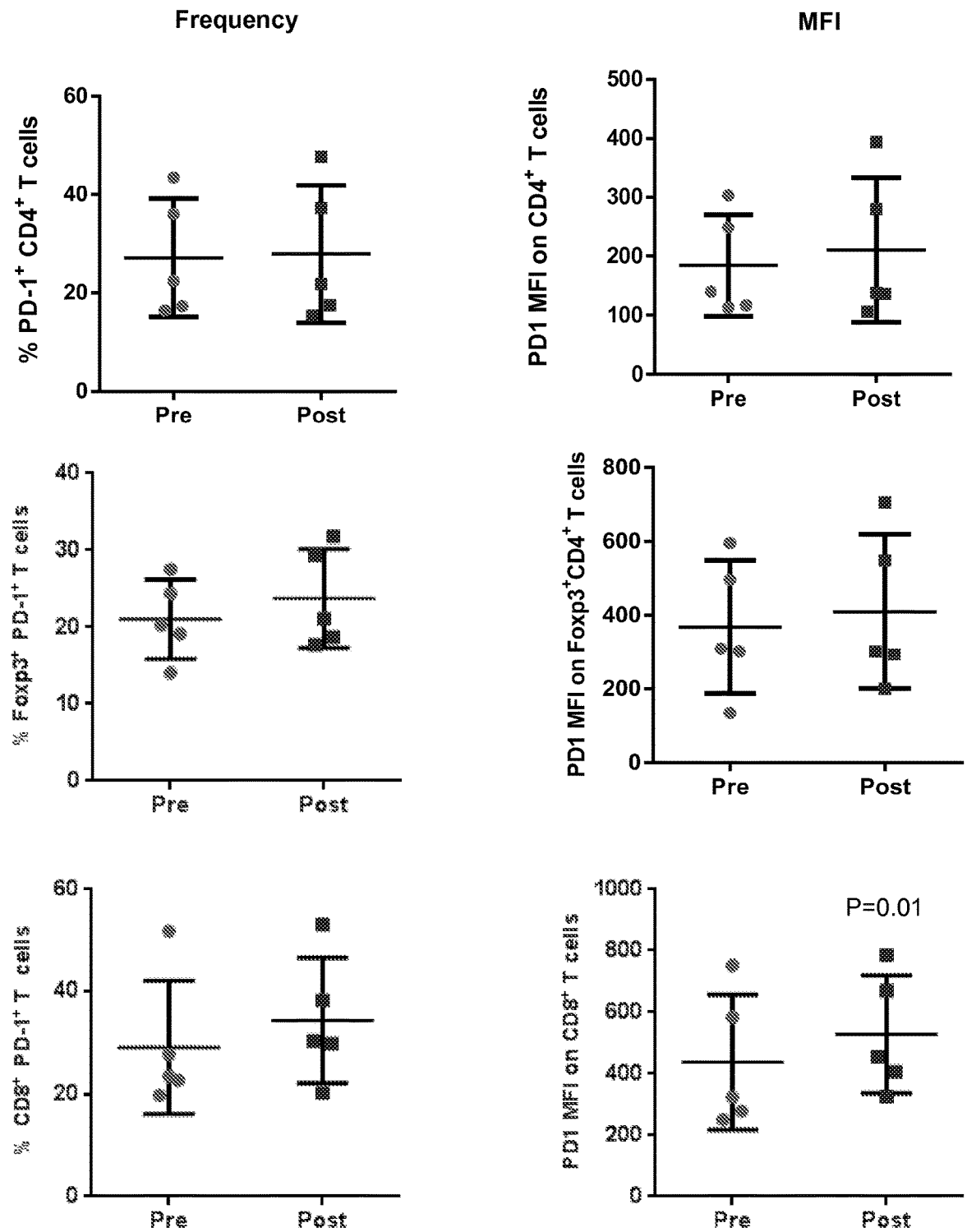

In this example, PD-1 status was evaluated in HCC patients who were being treated with sorafenib. When PD-1 levels were evaluated for these patients, they appeared to fall into two groups—one where the percent of PD-1$^+$ cells was decreased as was the level of PD-1 after the sorafenib treatment (tested in CD4$^+$ and FoxP3 cells), and the other in which the patients did not show a decrease in any parameter. The percent PD-1$^+$ cells and PD-1 levels for the two groups are shown in FIGS. 12A and 12B. The individual data points in the figures represent each patient.

Figure 13:
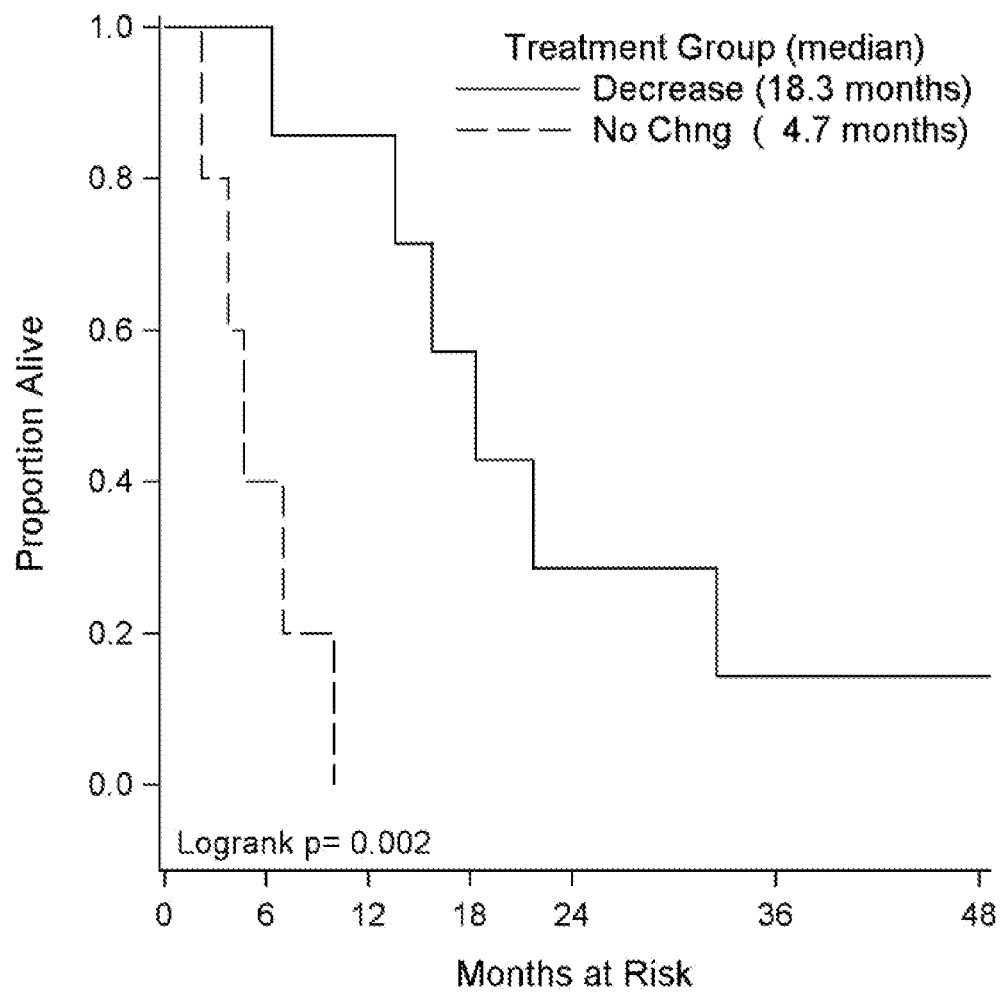
FIG. 13 shows survival curves for the two groups from FIGS. 6A and 6B.

Evaluation of survival data for these two groups indicated that the mean survival time for the group where PD-1 was decreased was 688 days and the mean survival for patients in the second group—which did not show a decrease in Pd-1 was 168 days. Thus, reduced PD-1 levels in sorafenib treated patients correlated favorably with longer survival time. Survival curves for the two groups are shown in FIG. 13.

Example 3

This example further describes a study in which we evaluated the immunomodulatory effect of sorafenib in advanced stage HCC patients and observed that decrease in immunosuppressive burden after sorafenib treatment was correlated with clinical outcome.

Patients and Methods

We have quantified programmed death-1$^+$ (PD-1$^+$) T cells, T regulatory cells (Tregs) and myeloid derived suppressor cells (MDSC) in the peripheral blood mononuclear cells (PBMC) of 19 HCC patients pre and post sorafenib treatment using multi-parametric flow cytometry. Plasma levels of both pro-inflammatory and immunosuppressive cytokines were determined by ELISA.

This study was approved by institutional review board of Roswell Park Cancer Institute (RPCI), Buffalo, N.Y. and informed consent was obtained from all participants. Heparinized peripheral blood samples were obtained from HCC patients before the initiation of sorafenib treatment and after four weeks or more of oral sorafenib treatment, through Data Bank and Biorepository at RPCI.

Biomarker Analysis

PBMCs were isolated immediately by Ficoll-Paque Plus density gradient centrifugation and cryopreserved. Plasma was isolated and stored at −80° C. and used for measurement of immunosuppressive and immunostimulatory cytokines as described previously. Frequency, phenotype and functionality of immune cells after blocking immune check points were analyzed by multi-parameter flow cytometry.

Results

We found a significant interaction term between sorafenib treatment and the absolute number of either CD4$^+$ PD-1$^+$ T cells or CD8$^+$ PD-1$^+$ T cells for overall survival of the patients (log-rank P<0.04; P<0.04 respectively). A significant decrease in the frequency (P<0.02) and absolute number (P<0.05) of Foxp3$^+$ Tregs was observed after sorafenib treatment and a statistically significant improvement in overall survival was noted in patients showing a greater decrease in the number of Foxp3$^+$ Tregs (log-rank P<0.01). Sorafenib treatment did not significantly impact either the frequency or number of CD11b$^+$CD33$^+$ MDSC; however patients who had greater decrease in the percentage or number of MDSC post sorafenib treatment had a better prognosis quantified based on AFT models (AFT β P<0.05, P<0.05 respectively). Even though a significant decrease in the levels of Treg derived cytokines IL-10 and TGF-β with concomitant increase in IFN-γ was detected after sorafenib treatment, none of these cytokines showed any significant association with clinical outcome.

Figure 14:
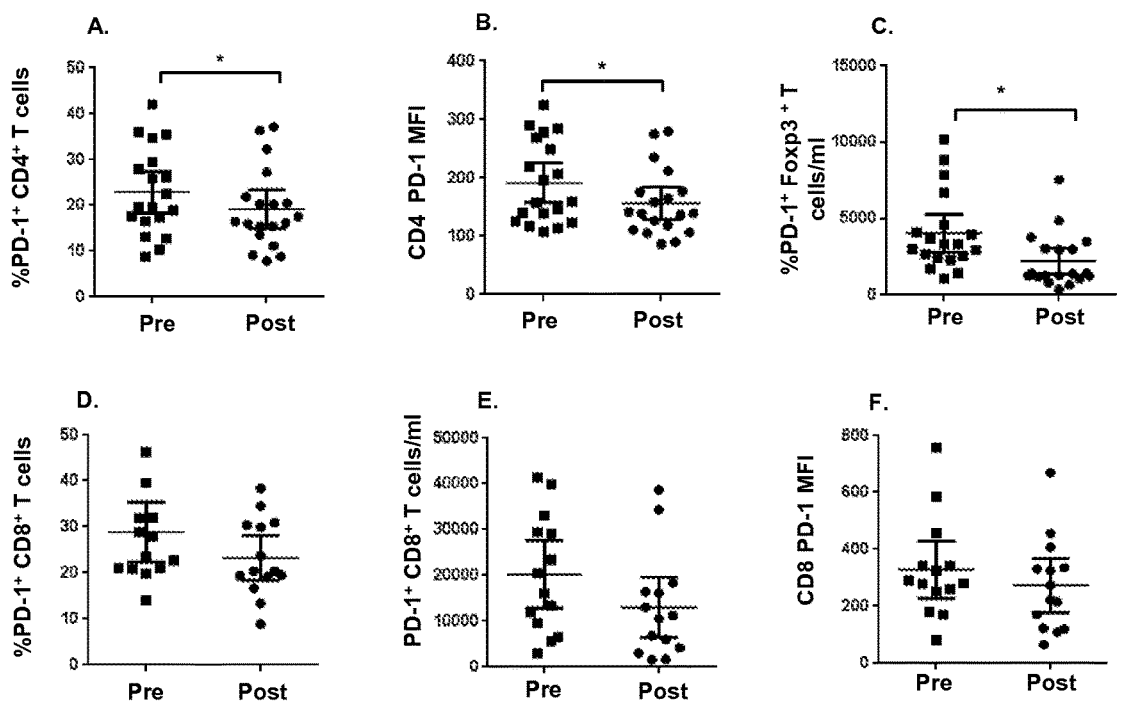
FIGS. 14A-14F. Decrease in PD-1⁺ T cells in HCC patients after sorafenib treatment.
Figure 15:
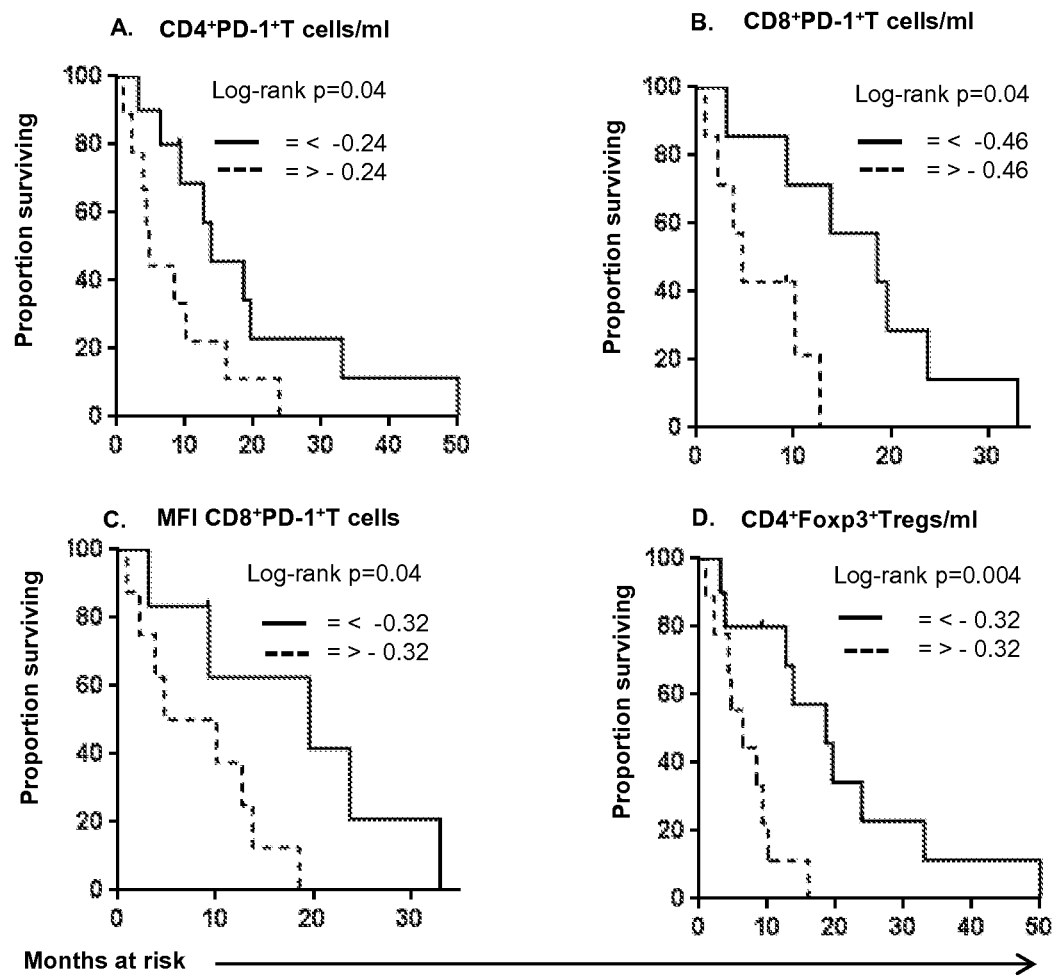
FIGS. 15A-15D. Kaplan-Meier plots showing the association of decrease in immnosuppressive cells and patient outcome after sorafenib treatment. Overall survival (OS) of HCC patients on the basis of greater decrease or smaller decrease in the absolute numbers of immunosuppressive cell types or their expression levels measured as MFI after sorafenib treatment. Patients were assessed for immune parameters before and after sorafenib treatment and stratified into greater decrease or smaller decrease group based on the median changes in immune parameters after sorafenib treatment. Overall survival of patients was calculated based on the status of (FIG. 15A) absolute numbers of $CD4^+PD-1^+$ T cells (FIG. 15B) $CD8^+PD-1^+$ T cells (FIG. 15C) expression levels of PD-1 (MFI) on $CD8^+$ T cells (FIG. 15D) absolute numbers of $CD4^+Foxp3^+$ T cells.

Reduction in PD-1+ T Cells Following Treatment with Sorafenib Correlates with Overall Survival We investigated the differential effect of sorafenib treatment on immune checkpoint receptor PD-1 expression on CD4+ T cells of HCC patients. The frequency of CD4+PD-1+ T cell was significantly reduced after sorafenib treatment (P<0.01, FIG. 14A, 95% CI, −5.72 to −1.05). The expression levels (measured as MFI) of PD-1 on CD4+ T cells were also significantly decreased (P<0.02, 95% CI, −56.51 to −12.09, FIG. 14B) after sorafenib treatment. Following sorafenib treatment, patients with greater decrease in the absolute number of PD-1+CD4+ T cells achieved significantly improved overall survival rate as compared to patients with smaller decrease in the absolute number of this phenotype (log-rank P<0.04 FIG. 15A). HCC patients with greater decrease in PD-1 expression levels after sorafenib treatment had a better overall survival benefit, quantified based on AFT models (AFT β P<0.04). Additionally, the absolute number of CD4+Foxp3+PD-1+ T cells after sorafenib treatment was significantly decreased (P<0.04; FIG. 14C).

The frequency and absolute number of CD8+PD-1+ T cells or the level of expression of PD-1 on CD8+ T cells as measured as MFI did not show any significant decrease after sorafenib treatment (P<0.20, P<0.15, P<0.31 respectively, FIG. 14D, FIG. 14E, FIG. 14F). However, we observed that patients who had a greater decrease either in the absolute number CD8+PD-1+ T cells or PD-1 expression levels on CD8+ T cells after sorafenib treatment achieved a significant improvement in overall survival when compared to patients who had a smaller decrease in either of these markers (log-rank P<0.04; P<0.04 respectively, FIG. 15B, FIG. 15C).

Sorafenib Treatment Reduces Number and Frequency of Tregs in HCC Patients with Survival Benefit We investigated the differential effect of sorafenib treatment on Treg numbers in HCC patients. A significant decrease in both the frequency and absolute numbers of CD3+CD4+Foxp3+ Tregs were observed in HCC patients' when measured after sorafenib treatment (P<0.02, P<0.05, 95% CI, −0.44 to −1.16 and −9.48 to −3.55 respectively, FIG. 16A, FIG. 16B). Absolute numbers of Tregs quantitated in PBMC obtained post-sorafenib treatment showed significant correlation with overall survival of the patient (log-rank P<0.01, FIG. 15D).

Levels of CTLA-4+ Foxp3+ Tregs after Sorafenib Treatment and Clinical Outcome

Figure 16:
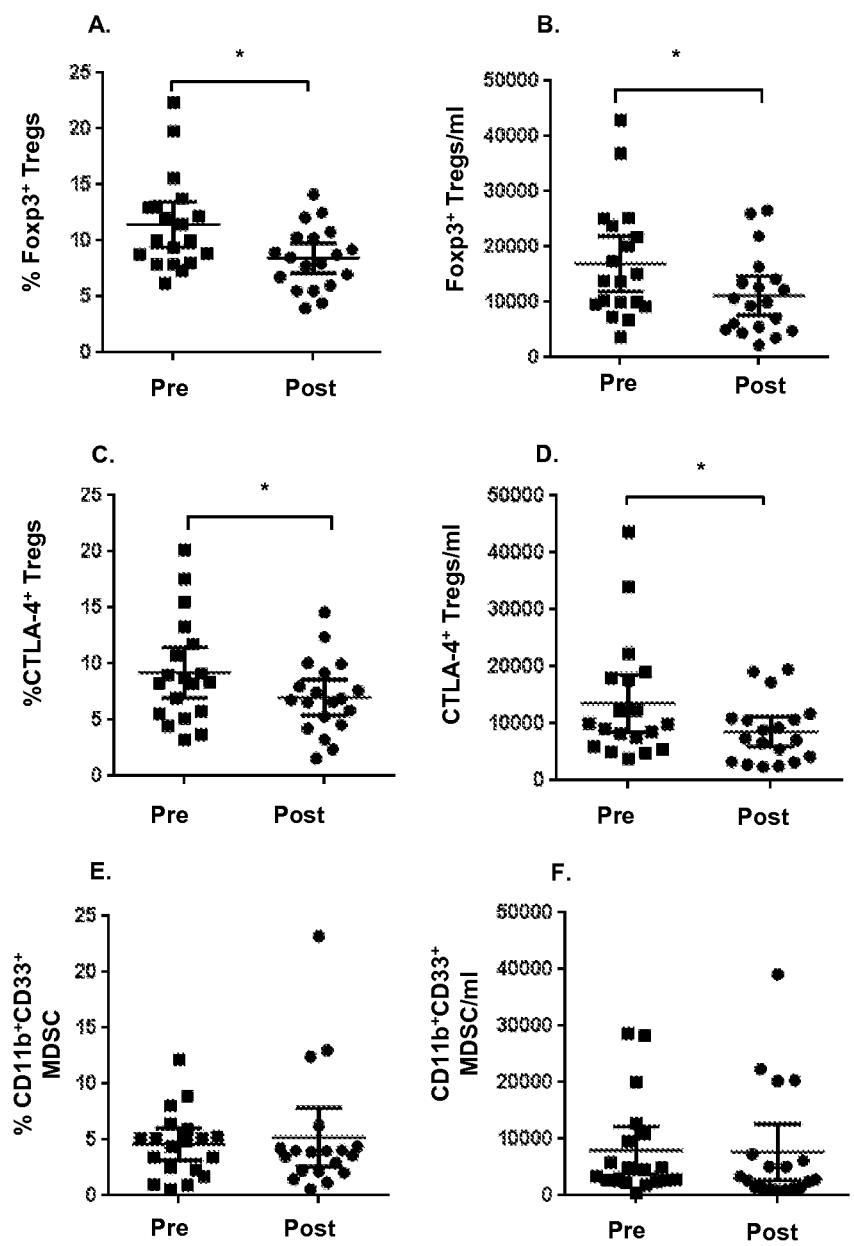
FIGS. 16A-16F. Decrease in Tregs and MDSC after sorafenib treatment in HCC patients.
Figure 18:
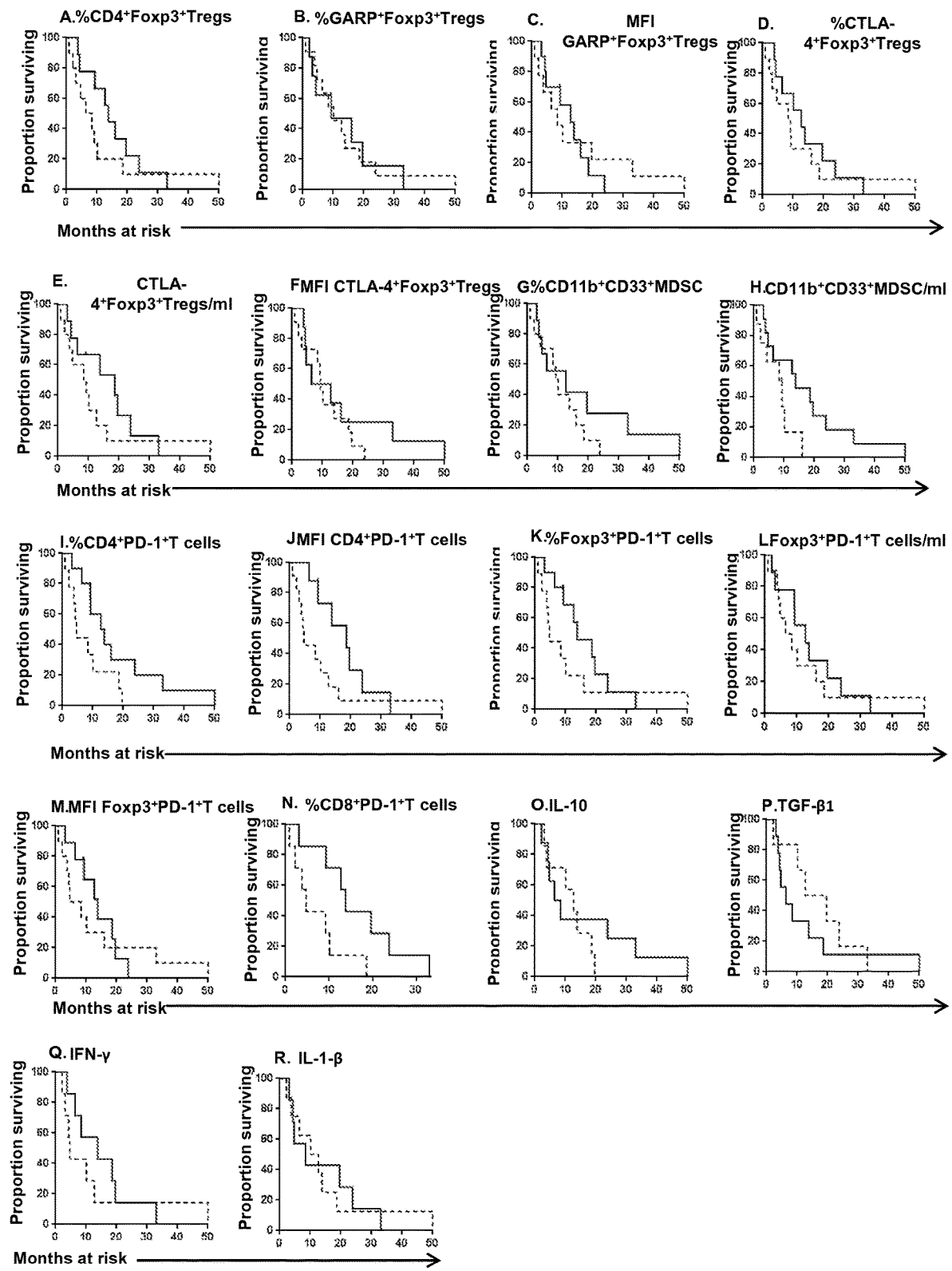
FIGS. 18A-18R. Kaplan-Meier plots showing the association of decrease in immnosuppressive cells and patient outcome after sorafenib treatment. Overall survival (OS) of HCC patients on the basis of greater decrease or smaller decrease in the frequency, absolute numbers of immunosuppressive cell types or their expression levels measured as MFI after sorafenib treatment. Patients were assessed for immune parameters before and after sorafenib treatment and stratified into greater decrease or smaller decrease group based on the median changes in immune parameters after sorafenib treatment. Overall survival of patients was calculated based on the status of (FIG. 18A) frequency of $CD4^+Foxp3^+$ Tregs (FIG. 18B) frequency of $GARP^+Foxp3^+$ Tregs (FIG. 18C) expression levels of GARP (MFI) on $Foxp3^+$ Tregs (FIG. 18D) frequency of $CTLA-4^+Foxp3^+$ Tregs (FIG. 18E) absolute number of $CD4^+Foxp3^+$ Tregs (FIG. 18F) expression levels of CTLA-4 (MFI) on $Foxp3^+$ Tregs (FIG. 18G) frequency of $CD11b^+CD33^+$ MDSC (FIG. 18H) absolute number of $CD11b^+CD33^+$ MDSC (FIG. 18I) frequency of $CD4^+PD-1^+$ T cells (FIG. 18J) expression levels of PD-1 (MFI) on $CD4^+$ T cells (FIG. 18K) frequency of $Foxp3^+PD-1^+$ T cells (FIG. 18L) absolute number of $Foxp3^+PD-1^+$ T cells (FIG. 18M) expression levels of PD-1 (MFI) on $Foxp3^+CD4^+$ T cells (FIG. 18N) frequency of $CD8^+PD-1^+$ T cells (FIG. 18O) IL-10 (FIG. 18P) TGF-β1 (FIG. 18Q) IFN-γ (FIG. 18R) IL-1β.
Figure 19:
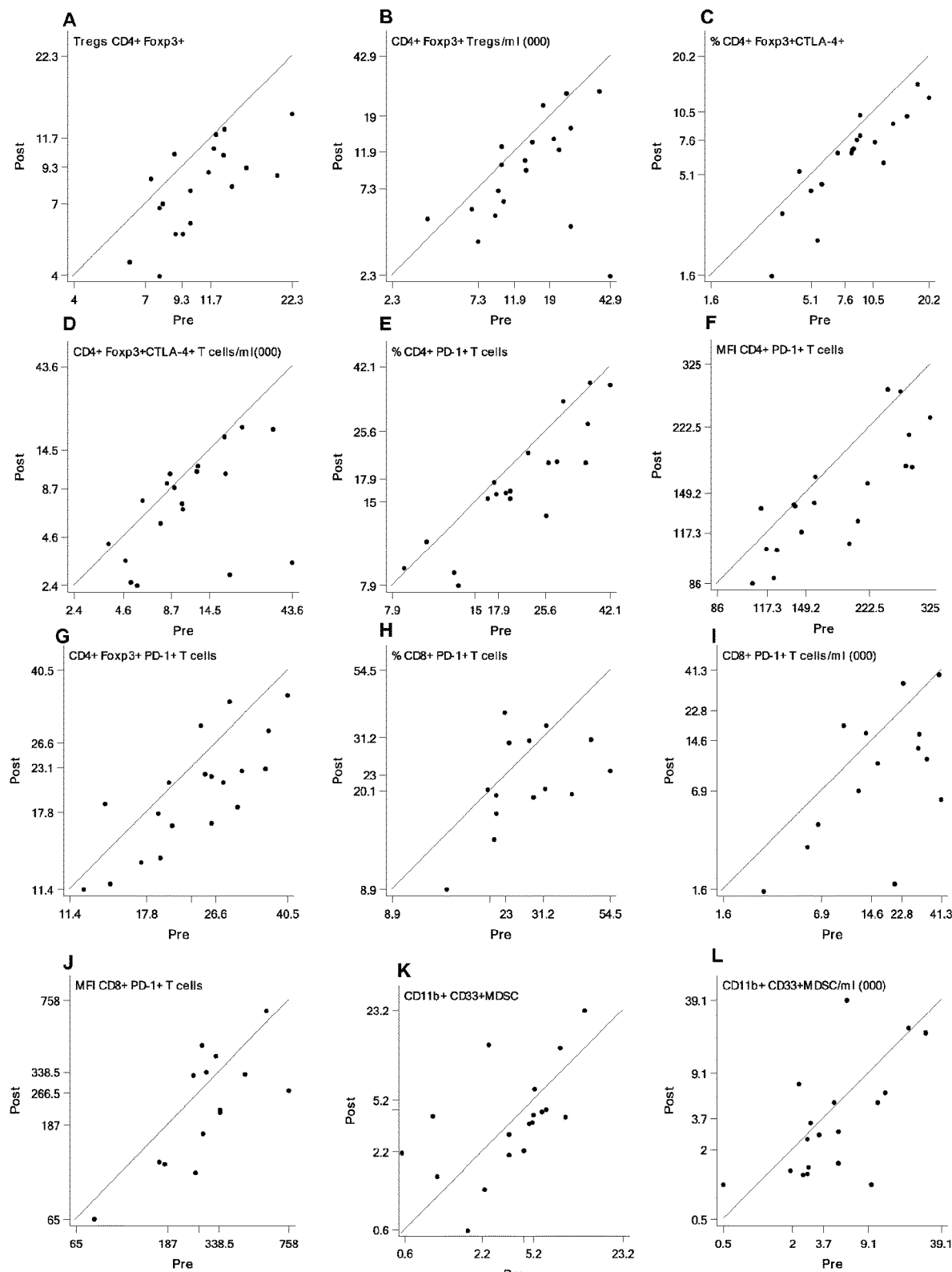
FIGS. 19A-19L. Agreement Plots showing the effect of sorafenib treatment on biomarker expression. Post treatment measurements of immune parameters were plotted against pretreatment measurements for HCC patients. Axes are log-scaled. The 45 degree line is known as the agreement line. In the absence of a treatment effect, measurement error and natural fluctuation, all of the points would fall on this line.
Figure 20:
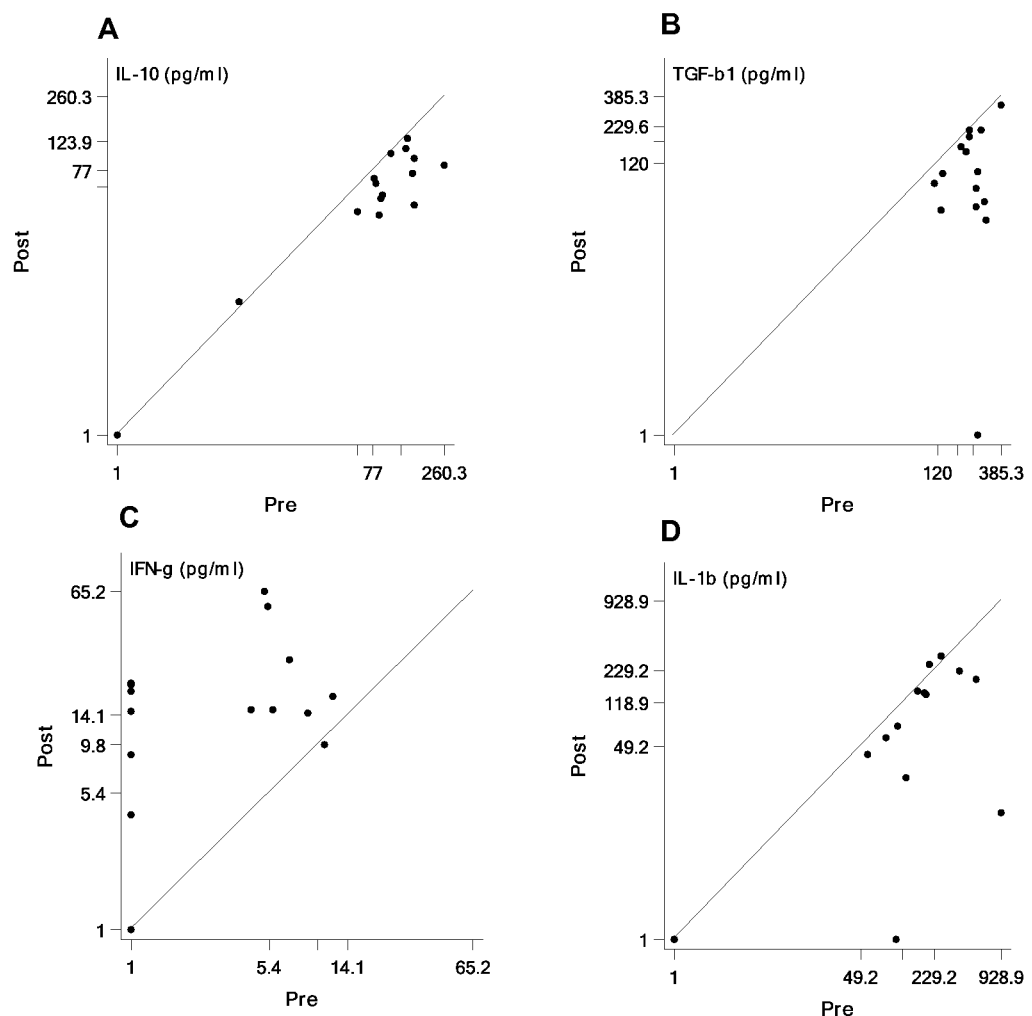
FIGS. 20A-20D. Agreement Plots showing the effect of sorafenib treatment on plasma cytokine levels. Post treatment measurements of plasma cytokine levels were plotted against pretreatment measurements for HCC patients. Axes are log-scaled. The 45 degree line is known as the agreement line. In the absence of a treatment effect, measurement error and natural fluctuation, all of the points would fall on this line. Levels of (FIG. 20A) IL-10 (FIG. 20B) TGF-β1 (FIG. 20C) IFN-γ (FIG. 20D) IL-1β. Each symbol represents an individual HCC patient pre and post sorafenib treatment (●).

Marked reduction in both the frequency and the absolute number of Foxp3+ CTLA-4+ Tregs was noted after sorafenib treatment (P<0.02, P<0.05, 95% CI, −3.18 to −0.82 and −8.42 to −6.32, FIG. 16C, FIG. 16D). However there were no significant differences in the overall survival in patients with greater decrease in the frequency or absolute number of CTLA-4+ Tregs when compared to those patients with smaller decrease in the frequency or absolute number of CTLA-4+ Tregs (log-rank P<0.51, P<0.30, FIG. 18D, FIG. 18E).

Effect of Sorafenib Treatment on MDSC Levels and Patient Survival

Sorafenib treatment did not have any significant influence either on the frequency or on the absolute number of CD11b+CD33+ MDSC in HCC patients (P<0.61; P<0.92, respectively, FIG. 16E, FIG. 16F). However, patients with greater decrease in the percentage and absolute number of MDSC after sorafenib treatment showed significant correlation with overall survival quantified based on AFT models (AFT β P<0.05, P<0.05 respectively).

Effect of Sorafenib Treatment on Cytokine Levels

Figure 17:
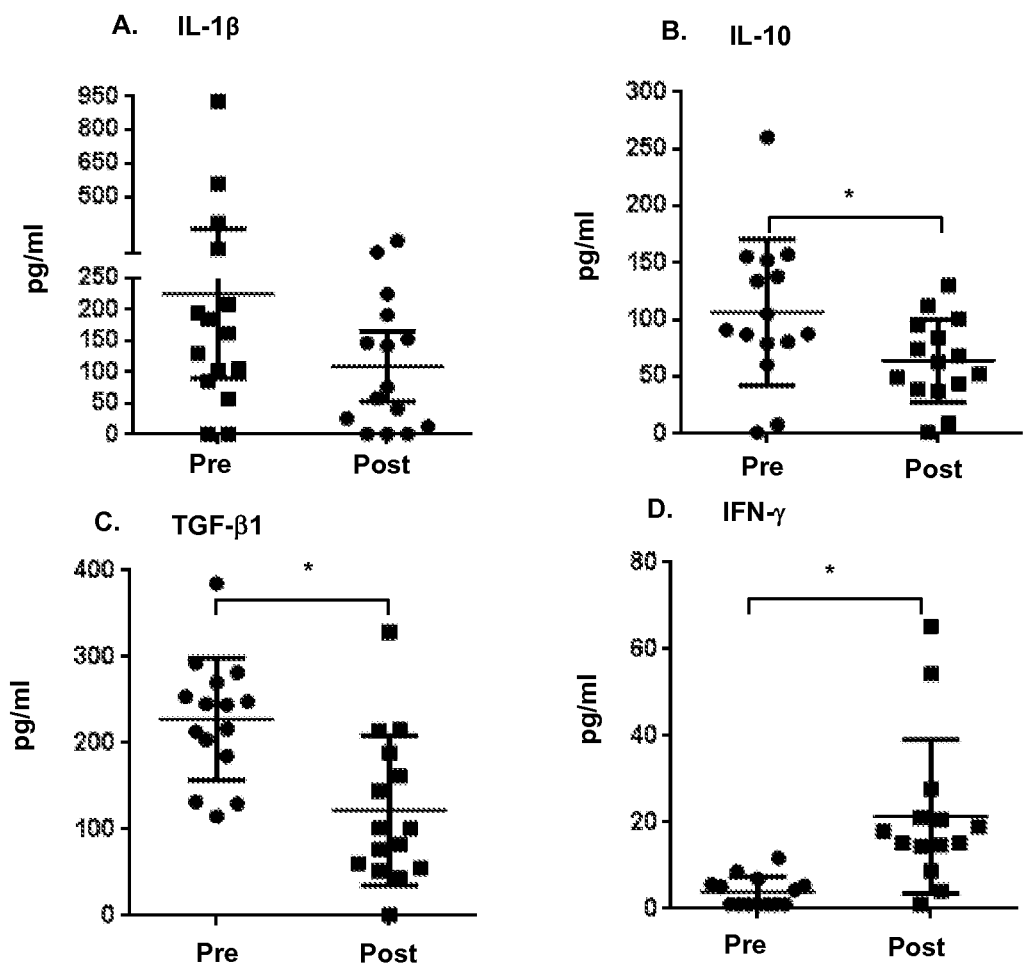
FIGS. 17A-17D. Changes in the levels of cytokines in HCC patients after sorafenib treatment. Cytokine-specific sandwich ELISA of plasma from HCC patients pre and post sorafenib treatment were carried out to measure the levels of circulating (FIG. 17A) IL-1β, (FIG. 17B) IL-10, (FIG. 17C) TGF-β1 and (FIG. 17D) IFN-γ. Each symbol represents an individual HCC patient pre (■) or post sorafenib treatment (●); lines represent mean values for the group. *P<0.05, Permutation t-test.

A significant decrease in the levels of immunosuppressive cytokines IL-10 and TGF-β1 were noted after sorafenib treatment (P<0.03; P<0.03, 95% CI −63.30 to −4.9; −151.50 to −48.55 respectively, FIG. 17B, FIG. 17C). The levels of proinflammatory cytokine IFN-γ were significantly increased after sorafenib treatment (P<0.04, 95% CI −1.07 to 23.64, FIG. 17D). The levels of IL-1β did not show any significant decrease in post-sorafenib treatment samples (P<0.11, FIG. 17A). We observed a non-significant interaction term between sorafenib treatment and changes in the levels of cytokines for overall survival of patients (log-rank P<0.73; P<0.61; P<0.62; P<0.92 respectively, FIG. 18O, FIG. 18P, FIG. 18Q, FIG. 18R). FIGS. 19A-19L suggest a decline in marker values following treatment. FIGS. 20A-20D suggest a decline in immunosuppressive cytokine levels and increase in IFN-γ levels following treatment.

While the disclosure is illustrated through specific examples, these examples are not intended to be restrictive and routine modifications to the various embodiments may be made by those skilled in the art.

The invention claimed is:

1. A method for alleviating the symptoms of or treating an individual diagnosed with advanced hepatocellular carcinoma (HCC) comprising the steps of:
   a) determining level of PD-1 on CD4+ or CD8+ T cells in a sample obtained from the individual, said sample comprising PBMCs;
   b) administering to the individual a first dosage of sorafenib for a period of 1 to 20 weeks;
   c) during the 1-20 weeks of administration of first dosage of sorafenib, periodically determining levels of PD-1 on CD4+ or CD8+ T cells, wherein a decrease in the PD-1 levels is indicative of improved survival;
   d) if a reduction in PD-1 levels is obtained, then initiating a regimen of a second dosage of sorafenib in combination with one or more PD-1 inhibitors, wherein the second dosage of sorafenib is lower than the first dosage of sorafenib.

2. The method of claim 1, wherein the PD-1 level is the level of expression of PD-1 on CD4+ or CD8+ T cells, or the percent of PD-1+ CD4+ T cells as a percent of total CD4+ T cells, or the percent of PD-1+ CD8+ T cells as a percent of total CD8+ T cells.

3. The method of claim 1, wherein the reduction in step d) is at least 10%.

4. The method of claim 1, wherein the first dose of sorafenib is from 300 to 500 mg.

5. The method of claim 4, wherein the first dose of sorafenib is 400 mg.

6. The method of claim 1, wherein the second dose of sorafenib is from 50 to 90% of the first dose.

7. The method of claim 5, wherein the second dose of sorafenib is from 50 to 90% of the first dose.

8. The method of claim 1, wherein the first dose of sorafenib is 300 to 500 mg and the second dose is from 100 to 250 mg.

9. The method of claim 1, wherein the first dose of sorafenib is 400 mg and the second dose is from 100 to 300 mg.

* * * * *